US008564780B2

(12) United States Patent
Walsh et al.

(10) Patent No.: US 8,564,780 B2
(45) Date of Patent: Oct. 22, 2013

(54) METHOD AND SYSTEM FOR USING REFLECTOMETRY BELOW DEEP ULTRA-VIOLET (DUV) WAVELENGTHS FOR MEASURING PROPERTIES OF DIFFRACTING OR SCATTERING STRUCTURES ON SUBSTRATE WORK PIECES

(75) Inventors: Phillip Walsh, Austin, TX (US); Dale Harrison, Austin, TX (US)

(73) Assignee: Jordan Valley Semiconductors Ltd., Migdal Haemek (IL)

( * ) Notice: Subject to any disclaimer, the term of this patent is extended or adjusted under 35 U.S.C. 154(b) by 471 days.

(21) Appl. No.: 12/844,851

(22) Filed: Jul. 28, 2010

(65) Prior Publication Data

US 2010/0290033 A1    Nov. 18, 2010

Related U.S. Application Data

(63) Continuation-in-part of application No. 12/080,947, filed on Apr. 7, 2008, now abandoned, and a continuation-in-part of application No. 12/590,151, filed on Nov. 3, 2009, now Pat. No. 8,014,000, which is a continuation of application No. 12/231,350, filed on Sep. 2, 2008, now abandoned, which is a continuation of application No. 11/517,894, filed on Sep. 8, 2006, now Pat. No. 7,446,876, which is a continuation of application No. 10/909,126, filed on Jul. 30, 2004, now Pat. No. 7,126,131, which is a continuation-in-part of application No. 10/668,642, filed on Sep. 23, 2003, now Pat. No. 7,067,818.

(60) Provisional application No. 60/440,434, filed on Jan. 16, 2003, provisional application No. 60/440,435, filed on Jan. 16, 2003, provisional application No. 60/440,443, filed on Jan. 16, 2003, provisional application No. 60/922,434, filed on Apr. 9, 2007.

(51) Int. Cl.
   *G01N 21/55*    (2006.01)

(52) U.S. Cl.
   USPC ........... 356/445; 356/328; 250/372; 250/339; 250/2

(58) Field of Classification Search
   USPC ...................... 356/445, 328; 250/372, 339.02
   See application file for complete search history.

(56) References Cited

U.S. PATENT DOCUMENTS 3,091,154 A    5/1963    Hall
3,160,752 A    12/1964    Bennett
(Continued)

FOREIGN PATENT DOCUMENTS

CN    2430682 Y    5/2001
JP    H08-022129 A    1/1996
(Continued)

OTHER PUBLICATIONS

U.S. Appl. No. 12/590,151 Official Action dated Mar. 17, 2011.
(Continued)

*Primary Examiner* — Tarifur Chowdhury
*Assistant Examiner* — Isiaka Akanbi
(74) *Attorney, Agent, or Firm* — D. Kligler I.P. Services Ltd.

(57) ABSTRACT

A method and apparatus is disclosed for using below deep ultra-violet (DUV) wavelength reflectometry for measuring properties of diffracting and/or scattering structures on semiconductor work-pieces is disclosed. The system can use polarized light in any incidence configuration, but one technique disclosed herein advantageously uses un-polarized light in a normal incidence configuration. The system thus provides enhanced optical measurement capabilities using below deep ultra-violet (DUV) radiation, while maintaining a small optical module that is easily integrated into other process tools. A further refinement utilizes an r-θ stage to further reduce the footprint.

26 Claims, 3 Drawing Sheets

(56) References Cited

U.S. PATENT DOCUMENTS

| | | |
|---|---|---|
| 3,572,951 A | 3/1971 | Rothwarf et al. |
| 3,751,643 A | 8/1973 | Dill et al. |
| 3,825,347 A | 7/1974 | Kaiser |
| 4,029,419 A | 6/1977 | Schumann et al. |
| 4,040,750 A | 8/1977 | Zwiener |
| 4,368,983 A | 1/1983 | Bennett |
| 4,645,349 A | 2/1987 | Tabata |
| 4,729,657 A | 3/1988 | Cooper et al. |
| 4,837,603 A | 6/1989 | Hayashi |
| 4,899,055 A | 2/1990 | Adams |
| 4,984,894 A | 1/1991 | Kondo |
| 5,042,949 A | 8/1991 | Greenberg et al. |
| 5,045,704 A | 9/1991 | Coates |
| 5,120,966 A | 6/1992 | Kondo |
| 5,128,549 A | 7/1992 | Kaya |
| 5,164,790 A | 11/1992 | McNeil et al. |
| 5,182,618 A | 1/1993 | Heinonen |
| 5,241,366 A | 8/1993 | Bevis et al. |
| 5,251,006 A | 10/1993 | Honigs et al. |
| 5,357,448 A | 10/1994 | Stanford |
| RE34,783 E | 11/1994 | Coates |
| 5,388,909 A | 2/1995 | Johnson et al. |
| 5,432,607 A | 7/1995 | Taubenblatt |
| 5,440,141 A | 8/1995 | Horie |
| 5,452,091 A | 9/1995 | Johnson |
| 5,486,701 A | 1/1996 | Norton et al. |
| 5,493,401 A | 2/1996 | Horie et al. |
| 5,581,350 A | 12/1996 | Chen et al. |
| 5,607,800 A | 3/1997 | Ziger |
| 5,608,526 A | 3/1997 | Piwonka-Corle et al. |
| 5,686,993 A | 11/1997 | Kokubo et al. |
| 5,703,692 A | 12/1997 | McNeil et al. |
| 5,739,909 A | 4/1998 | Blayo et al. |
| 5,747,813 A | 5/1998 | Norton et al. |
| 5,754,296 A | 5/1998 | Law |
| 5,771,094 A | 6/1998 | Carter et al. |
| 5,777,733 A | 7/1998 | Radziuk |
| 5,781,304 A | 7/1998 | Kotidis et al. |
| 5,784,167 A | 7/1998 | Ho |
| 5,798,837 A | 8/1998 | Aspnes et al. |
| 5,805,285 A | 9/1998 | Johs et al. |
| 5,835,225 A | 11/1998 | Thakur |
| 5,867,276 A | 2/1999 | McNeil et al. |
| 5,880,831 A | 3/1999 | Buermann et al. |
| 5,900,939 A | 5/1999 | Aspnes et al. |
| 5,903,351 A | 5/1999 | Jeong et al. |
| 5,917,594 A | 6/1999 | Norton |
| 5,963,329 A | 10/1999 | Conrad et al. |
| 5,991,022 A | 11/1999 | Buermann et al. |
| 6,052,401 A | 4/2000 | Wieser et al. |
| 6,091,485 A | 7/2000 | Li et al. |
| 6,122,052 A | 9/2000 | Barnes et al. |
| 6,128,085 A | 10/2000 | Buermann et al. |
| 6,129,807 A | 10/2000 | Grimbergen et al. |
| 6,181,427 B1 | 1/2001 | Yarussi et al. |
| 6,184,529 B1 | 2/2001 | Contini |
| 6,184,984 B1 | 2/2001 | Lee et al. |
| 6,226,086 B1 | 5/2001 | Holbrook et al. |
| 6,261,853 B1 | 7/2001 | Howell et al. |
| 6,265,033 B1 | 7/2001 | Hilliard |
| 6,275,292 B1 | 8/2001 | Thakur et al. |
| 6,278,519 B1 | 8/2001 | Rosencwaig et al. |
| 6,281,674 B1 | 8/2001 | Huang |
| 6,296,984 B1 * | 10/2001 | Gabor et al. ............... 430/270.1 |
| 6,297,880 B1 | 10/2001 | Rosencwaig et al. |
| 6,304,326 B1 | 10/2001 | Aspnes et al. |
| 6,313,466 B1 | 11/2001 | Olsen et al. |
| 6,327,035 B1 | 12/2001 | Li et al. |
| 6,340,602 B1 | 1/2002 | Johnson et al. |
| 6,361,646 B1 | 3/2002 | Bibby, Jr. et al. |
| 6,392,756 B1 | 5/2002 | Li et al. |
| 6,411,385 B2 | 6/2002 | Aspnes et al. |
| 6,414,302 B1 | 7/2002 | Freeouf |
| 6,417,921 B2 | 7/2002 | Rosencwaig et al. |
| 6,433,878 B1 | 8/2002 | Niu et al. |
| 6,453,006 B1 | 9/2002 | Koppel |
| 6,483,580 B1 | 11/2002 | Xu et al. |
| 6,485,872 B1 | 11/2002 | Rosenthal et al. |
| 6,503,693 B1 * | 1/2003 | Mohondro et al. ............ 430/328 |
| 6,525,829 B1 | 2/2003 | Powell et al. |
| 6,538,731 B2 | 3/2003 | Niu et al. |
| 6,549,279 B2 | 4/2003 | Adams et al. |
| 6,556,303 B1 | 4/2003 | Rangarajan et al. |
| 6,572,951 B2 | 6/2003 | Hasegawa et al. |
| 6,580,510 B2 | 6/2003 | Nawracala |
| 6,590,656 B2 | 7/2003 | Xu et al. |
| 6,608,690 B2 | 8/2003 | Niu et al. |
| 6,630,673 B2 | 10/2003 | Khalil et al. |
| 6,630,996 B2 | 10/2003 | Rao et al. |
| 6,633,831 B2 | 10/2003 | Nikoonahad et al. |
| 6,643,354 B2 | 11/2003 | Koppel et al. |
| 6,654,131 B2 | 11/2003 | Opsal et al. |
| 6,657,736 B1 | 12/2003 | Finarov et al. |
| 6,657,737 B2 | 12/2003 | Kimba et al. |
| 6,665,075 B2 | 12/2003 | Mittleman et al. |
| 6,673,637 B2 | 1/2004 | Wack et al. |
| 6,704,661 B1 | 3/2004 | Opsal et al. |
| 6,710,865 B2 | 3/2004 | Forouhi et al. |
| 6,713,753 B1 | 3/2004 | Rovira et al. |
| 6,713,775 B2 | 3/2004 | Chelvayohan et al. |
| 6,721,052 B2 | 4/2004 | Zhao et al. |
| 6,734,968 B1 | 5/2004 | Wang et al. |
| 6,765,676 B1 | 7/2004 | Buermann |
| 6,768,785 B2 | 7/2004 | Koppel |
| 6,768,967 B2 | 7/2004 | Johnson et al. |
| 6,775,015 B2 | 8/2004 | Bischoff et al. |
| 6,778,273 B2 | 8/2004 | Norton et al. |
| 6,778,911 B2 | 8/2004 | Opsal et al. |
| 6,801,309 B1 | 10/2004 | Nelson |
| 6,806,951 B2 | 10/2004 | Wack et al. |
| 6,806,971 B2 | 10/2004 | Finarov |
| 6,813,034 B2 | 11/2004 | Rosenewaig et al. |
| 6,819,426 B2 | 11/2004 | Sezginer et al. |
| 6,856,408 B2 | 2/2005 | Raymon |
| 6,879,395 B2 | 4/2005 | Oka et al. |
| 6,891,626 B2 | 5/2005 | Niu et al. |
| 6,897,456 B2 | 5/2005 | Hasegawa et al. |
| 6,897,807 B2 | 5/2005 | Kishigami et al. |
| 6,898,537 B1 | 5/2005 | McGahan |
| 6,909,507 B2 | 6/2005 | Norton et al. |
| 6,917,419 B2 | 7/2005 | Fielden et al. |
| 6,919,957 B2 | 7/2005 | Nikoonahad et al. |
| 6,934,025 B2 | 8/2005 | Opsal et al. |
| 6,979,578 B2 | 12/2005 | Venugopal |
| 6,982,792 B1 | 1/2006 | Woollam et al. |
| 6,987,832 B2 | 1/2006 | Koppel et al. |
| 7,006,235 B2 | 2/2006 | Levy et al. |
| 7,026,165 B2 | 4/2006 | DeGrandpre |
| 7,026,626 B2 | 4/2006 | Harrison |
| 7,030,999 B2 | 4/2006 | Bischoff et al. |
| 7,031,894 B2 | 4/2006 | Niu et al. |
| 7,046,375 B2 | 5/2006 | Bischoff et al. |
| 7,049,156 B2 | 5/2006 | Kueny |
| 7,053,991 B2 | 5/2006 | Sandusky |
| 7,061,614 B2 | 6/2006 | Wang et al. |
| 7,067,818 B2 | 6/2006 | Harrison |
| 7,068,363 B2 | 6/2006 | Bevis et al. |
| 7,072,050 B2 | 7/2006 | Kimba et al. |
| 7,095,511 B2 | 8/2006 | Chalmers et al. |
| 7,126,131 B2 | 10/2006 | Harrison |
| 7,130,029 B2 | 10/2006 | Wack et al. |
| 7,189,973 B2 | 3/2007 | Harrison |
| 7,196,785 B2 | 3/2007 | Nishiyama et al. |
| 7,224,471 B2 | 5/2007 | Bischoff et al. |
| 7,242,477 B2 | 7/2007 | Mieher et al. |
| 7,271,394 B2 | 9/2007 | Harrison |
| 7,282,703 B2 | 10/2007 | Walsh et al. |
| 7,342,235 B1 | 3/2008 | Harrison et al. |
| 7,349,079 B2 | 3/2008 | Zhao et al. |
| 7,359,052 B2 | 4/2008 | Fielden et al. |
| 7,391,030 B2 | 6/2008 | Harrison |
| 7,391,524 B1 | 6/2008 | Chen et al. |
| 7,394,551 B2 | 7/2008 | Harrison |
| 7,399,975 B2 | 7/2008 | Harrison |

(56) References Cited

U.S. PATENT DOCUMENTS

| | | | |
|---|---|---|---|
| 7,446,876 | B2 | 11/2008 | Harrison |
| 7,485,869 | B2 | 2/2009 | Harrison et al. |
| 7,511,265 | B2 | 3/2009 | Walsh et al. |
| 7,579,601 | B2 | 8/2009 | Harrison et al. |
| 7,643,666 | B2 | 1/2010 | Setija et al. |
| 7,684,037 | B2 | 3/2010 | Harrison |
| 2001/0055118 | A1 | 12/2001 | Nawracala |
| 2002/0030826 | A1 | 3/2002 | Chalmers et al. |
| 2002/0088952 | A1 | 7/2002 | Rao et al. |
| 2002/0126277 | A1 | 9/2002 | Norton et al. |
| 2002/0149774 | A1 | 10/2002 | McAninch |
| 2002/0154302 | A1 | 10/2002 | Rosencwaig et al. |
| 2002/0190207 | A1 | 12/2002 | Levy et al. |
| 2003/0071996 | A1 | 4/2003 | Wang et al. |
| 2003/0081201 | A1 | 5/2003 | Shibata et al. |
| 2004/0150820 | A1 | 8/2004 | Nikoonahad et al. |
| 2005/0001172 | A1 | 1/2005 | Harrison |
| 2005/0036143 | A1 | 2/2005 | Huang |
| 2006/0001885 | A1 | 1/2006 | Hertzsch et al. |
| 2006/0066855 | A1 | 3/2006 | Boef et al. |
| 2007/0181793 | A1 | 8/2007 | Harrison |
| 2007/0215801 | A1 | 9/2007 | Walsh et al. |
| 2008/0073560 | A1 | 3/2008 | Harrison et al. |
| 2008/0129986 | A1 | 6/2008 | Walsh |
| 2008/0181793 | A1 | 7/2008 | Mistry et al. |
| 2008/0246951 | A1 | 10/2008 | Walsh et al. |
| 2009/0002711 | A1 | 1/2009 | Harrison |
| 2009/0248074 | A1 | 10/2009 | Kliegman et al. |
| 2010/0051822 | A1 | 3/2010 | Harrison |

FOREIGN PATENT DOCUMENTS

| | | | |
|---|---|---|---|
| JP | 10160572 | A | 6/1998 |
| JP | H10-160572 | A | 6/1998 |
| JP | 2000205966 | | 7/2000 |
| JP | 2000249600 | | 9/2000 |
| JP | 2002243381 | | 8/2002 |
| JP | 2003202266 | A | 7/2003 |
| JP | 2003232681 | A | 8/2003 |
| WO | 9902970 | A1 | 1/1999 |
| WO | 2007126612 | A2 | 11/2007 |
| WO | 2007130295 | A2 | 11/2007 |

OTHER PUBLICATIONS

U.S. Appl. No. 12/876,242 Official Action dated May 20, 2011.
U.S. Appl. No. 12/834,939 Official Action dated Jun. 10, 2011.
Japanese Patent Application # 2009507685 Office Action dated Apr. 3, 2012.
European Patent Application # 04784655.5 Search dated Jun. 27, 2012.
Bai et al., "Group Theoretic Approach to the Enhancement of the Fourier Method for grossed Gratings: C2 Symmetry Case", Optical Society of America, vol. 22, No. 4, pp. 654-651, Apr. 2005.
Bai et al., "Reduction of Computation Time for Crossed Gratings Problems: A Group Theoretic Approach", Optical Society of America, vol. 21, No. 10, pp. 1886-1894, Oct. 2004.
Li, L., "Use of Fouler Series in the Analysis of Discontinuous Periodic Structure", Optical Society of America, vol. 13, No. 9, pp. 1870-1876, Sep. 1996.
Granet et al., "Efficient Implementation of the Coupled Wave Method for Metallic Lamellar Gratings in TM Polarization", Optical Society of America, vol. 13, No. 5, pp. 1019-1023, May 1996.
Lalanne et al., "Highly Improved Convergence of the Coupled Wave Method for TM Polarization", Optical Society of America, vol. 13, No. 4, pp. 779-784, Apr. 1996.
Tan, E, "Enhanced R Matrix Algorithms for Multilayered Diffraction Gratings", Applied Optics, vol. 45, No. 20, pp. 4803-4809, Jul. 19, 2006.
Kaplan et al., "Characterization of Bidimensional Gratings by Spectroscopic Ellipsometry and Angle Resolved Mueller Polarimetry", Applied Optics, vol. 43, No. 6, pp. 1233-1240, Feb. 20, 2004.
Novikova et al., "Application of Mueller Polarimetry in Conical Diffraction for Critical Dimension Measurements in Microelectronics,", Applied Optics, vol. 45, No. 16, pp. 3688-3697, Jun. 1, 2006.
Bao, J., "An Optical Metrology System for Lithography Process Monitoring and Control", Thesis, University of California at Berkeley, Department of Electrical Engineering and Computer Sciences, 135 pages, Spring 2003.
Coulombe et al., "Ellipsometric—Scatterometry for Sub-01um CD Measurements" SPIE: vol. 3332, pp. 282-2393, year 1998.
Opsal et al "Fundamental Solutions for Real-Time Optical CD Metrology", SPIE, vol. 4689, pp. 63-176, year 2002.
Bischoff et al., "New Aspects of Optical Scatterometry Applied to Microtechnology", SPE, vol. 3215, pp. 144-155, year 1997.
Minhas et al., "Towards Sub-01 um CD Measurements Using Scatterometry", SPIE, vol. 2725, pp. 729-739, year 1996.
Bischoff et al., "Single Feature Metrology by Means for Light Scatter Analysis", SPIE, vol. 3050, pp. 574-585, year 1997.
Mills et al., "Spectral Elipsometry on Patters Wafers", SPIE, vol. 2637, pp. 194-203, year 1995.
Depine et al., "Internal Symmetries in Conical Diffraction from Metallic Gratings", Journal of Modern Optics, vol. 48, No. 8, pp. 1405-1411, year 2001.
Xie et al., "Transmission of tight Through Periodic Arrays of Sub-Wavelength Slits in Metailic Hosts", Optics Express, vol. 14, No. 14, pp. 6400-6413, Jul. 10, 2006.
Robert et al., "Control of the Homogeneity of an Optical Grating by a Neural Characterization" Optical Engineering, vol. 44, No. 3, 5 pages, Mar. 2005.
Boyer et al., "Diffraction Theory: Application of the Fast Fourier Factorization to Cylindrical Devices with Arbitrary Cross Section Lighted in Conical Mounting", Optical Society of America, vol. 23. No. 5, pp. 1146-1158, May 2006.
Cordeiro et al., "Phase Constraint for the Waves Diffracted by Lossless Symmetrical Gratings at Littrow Mount", Optical Society of America, vol. 23, No. 1, pp. 166-171, Jan. 2006.
Robert et al., "Experimental Characterization of Subwavelength Diffraction Gratings by an Inverse-Scattering Neural Method", Optical Society of America, vol. 19, No. 12, pp. 2394-2402, Dec. 2002.
Robert et al., "Characterization of Optical Diffraction Gratings by Use of a Neural Method", Optical Society of America, vol. 19, No. 1, pp. 24-32, Jan. 2002.
Li, L., "Symmetries of Cross-Polarization Diffraction Coefficients of Gratings", Optical Society of Arnerica, vol. 17, No. 5, pp. 881-887, May 2000.
Logofatu et al., "identity of the Cross-Reflection Coefficients for Symmetric Surface Relief Gratings", Optical Society of America, vol. 16, No. 5, pp. 1108-1114, May 1999.
Zolla et al., "Method of Fictitious Sources as Applied to the Electromagnetic Diffraction of a Plane Wave by a Grating in Conical Diffraction Mounts", Optical Society of America, vol. 13, No. 4, pp. 796-802, Apr. 1996.
Peng et al., "Efficient Implementation of Rigorous Coupled-Wave Analysis for Surface-Relief Gratings", Optical Society of America, vol. 12, No. 5, pp. 1087-1096, May 1995.
Li, L., "Multilayer Modal Method for Diffraction Gratings of Arbitrary Profile, Depth and Permittivity", Optical Society of America, vol. 10, No. 12, pp. 2581-2591, Dec. 1993.
Li et al., "Convergence of the Coupled-Wave Method for Metallic amellar Diffraction Gratings", Optical Society of America, vol. 10, No. 6, pp. 1184-1189, Jun. 1993.
Peng, S., "Rigorous Formulation of Scattering and Guidance by Dielectric Grating Waveguides: General Case of Oblique Incidence", Optical Society of America, vol. 6, No. 12, pp. 1869-1883, Dec. 1989.
Moharam et al., "Rigorous Coupled-Wave Analysis of Grating Diffraction-E-mode Polarization and Losses", Optical Society of America, vol. 73, No. 4, pp. 451-455, Apr. 1983.
Moharam et al., "Diffraction Analysis of Dielectric Surface Relief Gratings", Optical Society of America, vol. 72, No. 10, pp. 1385-1392, Oct. 1982.
Moharam et al., "Rigorous Coupled-Wave Analysis of Planar-Grating Diffraction", Optical Society of America, vol. 71, No. 7, pp. 811-818, Jul. 1981.

(56) References Cited

OTHER PUBLICATIONS

Knop, K., "Rigorous Diffraction Theory for Transmission Phase Gratings with Deep Rectangular Grooves", Optical Society of America, vol. 68, No. 9, pp. 1206-1210, Sep. 1978.
Kong, J., "Second-Order Coupled-Mode Equations for Spatially Periodic Media", Optical Society of America, vol. 67, No. 6, pp. 825-829, Jun. 1977.
Azzam et al., "Generalized Ellipsometry for Surfaces with Directional Preference: Application to Diffraction Gratings", Journal of the Optical Society of America, vol. 62, No. 12, pp. 1521-1530, Dec. 1972.
Case, S., "Coupled-Wave Theory for Multiply Exposed Thick Holographic Gratings", Optical Society of America, vol. 65, No. 6,pp. 724-729, Jun. 1975.
Kaspar, F., "Diffraction by Thick, Periodically Stratified Gratings with Complex Dielectric Constant", Journal of Optical Society of America, vol. 63, No. 1, pp. 37-45, Jan. 1973.
Azzam et al., "Application of Generalized Ellipsometry to Anisotropic Crystals", Journal Optical Society of America, vol. 64, No. 2, pp. 128-133, Feb. 1974.
Burckhardt, C., "Diffraction of a Plane Wave at a Sinusoidally Stratified Dielectric Grating", Journal of Optical Society of America, vol. 56, No. 11, pp. 1502-1509, Nov. 1966.
Krukar et al., "Reactive Ion Etching Profile and Depth Characterization Using Statistical and Neural Network Analysis of Light Scattering Data", American Institute of Physics, vol. 74, No. 6, pp. 3698-3706, Sep. 15, 1993.
Li, L., "A Modal Analysis of Lamellar Diffraction Gratings in Conical Mountings", Journal of Modern Optics, vol. 40, No. 4, pp. 553-573, year 1993.
Momeni et al., "Pure Coupled Mode Analysis of Diffraction by Isotropic Transmission Volume Gratings", IEEE Transactions on Antennas and Propagation, vol. 52, No. 12, pp. 3304-3311, Dec. 2004.
Momeni et al., "Improved Coupled Wave Analysis of Two-Dimensional Planar Multiple Gratings", IEEE Transactions on Antennas and Propagation, vol. 52, No. 1, pp. 165-171, Jan. 2004.
Garnaes et al., "Profiles of a High-Aspect Radio Grating Determined by Spectroscopic Scatterometry and Atomic-Force Microscopy", Applied Optics, vol. 45, No. 14, pp. 3201-3212, May 10, 2006.
Kallioniemi et al., "Characterization of Diffraction Gratings in a Rigorous Domain with Optical Scatterometry: Hierarchical Neural-Network Model", Applied Optics, vol. 38, No. 28, pp. 5920-5930, Oct. 1, 1999.
Ahmed et al., "Comparison of Beam Propagation Method and Rigorous Coupled-Wave Analysis for Single and Multiplexed Volume Gratings", Applied Optics, vol. 35, No. 22, pp. 4426-4435, Aug. 1, 1996.
Minhas at al., "Ellipsometric Scatterometry for the Metrology of Sub-01-um-linewidth Structures", Applied Optics, vol. 37, No. 22, pp. 5112-5115, Aug. 1, 1998.
Kallioniemi at al., "Optical Scatterometry of Subwavelength Diffraction Gratings: Neural Network Approach", Applied Optics, vol. 37, No. 25, pp. 5830-5835, Sep. 1, 1998.
Huang et al., "Normal-Incidence Spectroscopic Ellipsometry for Critical Dimension Monitoring", Applied Physics Letters, vol. 78, No. 25, pp. 3893-3985, Jun. 18, 2001.
U.S. Appl. No. 12/592,773 Official Action dated Sep. 1, 2010.
U.S. Appl. No. 12/834,939 Official Action dated Oct. 29, 2010.
Press et al., "Numerical Recipes in C: 15.5 Non-Linear models", The Art of Scientific Computing, Second Edition, 15.5 Non-Linear models, pp. 661-686, Cambridge University Press 2002.
U.S. Appl. No. 12/080,947 (abandoned) Official Action dated Mar. 30, 2010.
Bai et al., "Group Theoretic Approach to Enhancing the Fourier Method for Crossed Gratings with Square Symmetry", Optical Society of America, vol. 23, No. 3, pp. 572-560, Mar. 2006.
Tan, E., "Hybrid-Matrix Algorithm for Rigorous Coupled-Wave Analysis of Multilayered Diffraction Gratings", Journal of Modern Optics, vol. 53, No. 4, pp. 417-428, Mar. 10, 2006.
Das et al., "Image Evaluation of the High-Resolution VUV Spectrometer at SURF II by Ray Tracing", Journal of Research of the National Institute of Standards and Technology, vol. 103, No. 5, pp. 483-495, Sep.-Oct. 1998.
US Re-Examination Application # 90/009,409 Official Action dated Jun. 18, 2010.
Chinese Patent Application No. 200480027513.6 Official Action dated Jul. 18, 2008.
US Re-Examination Application # 90/009,320 Official Action dated Sep. 25, 2009, and Notice of Intent to Issue Re-Exam Certificate dated Jun. 23, 2010.
Aspnes, D.E., "Determination of Optical Properties by Ellipsometry", Handbook of Optical Constants of Solids, vol. 1, pp. 104-108, Academic Press, 1998.
Bloomstein et al., "Contamination Rates of Optical Surface at 157nm in the Presence of Hydrocarbon impurities", Optical Microlithography XV, Proceedings of the SPIE, vol. 4691, pp. 709-723, Jul. 30, 2002.
Field et al., "Method of Using the Reflectance Ratios of Difference Angles of incidence for the Determination of Optical Constants", Applied Optics, vol. 10, No. 6, pp. 1402-1405, Jun. 1971.
Hunter, W., "Errors in Using the Reflectance vs Angie of Incidence Method for Measuring Optical Constants", Journal of the Optical Society of America, vol. 55, No. 10, part 1, pp. 1197-1204, Oct. 1965.
Hunter et al., "Thickness of Absorbing Films Necessary to Measure Their Optical Constants Using the Reflectance-Vs-Angle-of-Incidence Method", Journal of the Optical Society of America, vol. 84, No. 4, pp. 429-433, Apr. 1974.
Jellison et al., "Parameterization of the Optical Functions of Amorphous Materials in the Interband Region", Applied Physics Letter, Jul. 15, 1996 (vol. 69, No. 3. pp. 371-373), and Sep. 30, 1996 (vol. 69, No. 14, p. 2137).
Okoroanyanwu et al., "Contamination Monitoring and Control on ASML MS-VII 157nm Exposure Tool", Optical Microlithography XVII, Proceedings of the SPIE, vol. 5377, pp. 1695-1707, May 28, 2004.
International Application PCT/US2004/030650 Search Report dated Feb. 24, 2005.
Rivas, C., "Optical Characterization of Hafnium-Based High-K Dielectric Films Using Vacuum Ultraviolet Reflectometry", Proceedings of the XV International Conference on Vacuum Ultraviolet Radiation Physics, Berlin, Germany Jul. 29-Aug. 3, 2007.
International Application PCT/US2007/010003 Search Report issued Dec. 17, 2008.
U.S. Appl. No. 10/930,339 Official Action dated Sep. 29, 2009.
U.S. Appl. No. 10/930,339 Official Action dated Jan. 18, 2007.
U.S. Appl. No. 10/930,339 Official Action dated Sep. 6, 2007.
U.S. Appl. No. 10/930,339 Official Action dated Apr. 18, 2008.
U.S. Appl. No. 10/930,339 Official Action dated Nov. 13, 2008.
U.S. Appl. No. 12/454 837 "Automated Calibration Methodolog for VUV Metrology System" filed on May 22, 2009.
Visentine, J., "Optical Characterization of Molecular Contaminant Films", Photonics Tech Briefs, Jan. 1, 2007.
U.S. Appl. No. 12/592,641 Official Action dated Aug. 20, 2010.
Japanese Patent Application # 528098/06 Official Action dated Jun. 15, 2010 (including English translation).
US Re-Examination Application # 95/000,535 Official Action dated May 14, 2010.
Acton Research Corporation, "Acton Research Purged CAMS Optical Measurement System", Acton Research Product Brochure, USA, Published prior to Sep. 23, 2003.
McPherson Inc., "Reflectometer for Sample Analysis", McPherson Product Brochure, USA, Published prior to Sep. 23, 2003.
McPherson Inc., "Spectral Reflectometer", McPherson Product Brochure; USA, Nov. 12, 2001.
McPherson Inc., "VUVaS Spectrophotometers for 115 nm to >380nm", McPherson Product Brochure, USA, published prior to Sep. 23, 2003.
McPherson Inc., "VUVaS Spectrophotometers. Made to Measure 115-380 nm", McPherson Product Brochure, USA, published prior to Sep. 23, 2003.
Rubloff, G.W., "Surface Reflectance Spectroscopy System", Technical Disclosure, ip.com, May 1, 1977.

(56) References Cited

OTHER PUBLICATIONS

Sopra., "SE and GXR combined on the same instrument", printed from www.sopra-sa.com on Feb. 19, 2002.
Sopra., "The Ideal Thin Film Characterization Unit for Development and Pilot Line Environment", printed from www.sopra-sa.com on Feb. 19, 2002.
Sopra., "The Thin Film Tool for Next Generation Lithography at 157 nm", printed from www.sopra-sa.com on Feb. 19, 2002.
U.S. Appl. No. 12/854,917 "Method and Apparatus for Accurate Calibration of VUV Reflectometer" filed Aug. 12, 2010.
U.S. Appl. No. 12/876,242 "Broad Band Referencing Reflectometer" filed Sep. 7, 2010.
Sentech Instruments GmbH., "Vacuum UV Spectroscopic Ellipsometers", printed from www.sentech.de on Feb. 20, 2002.
J.A. Woolam Company, "Award Winning VUV-VASE is the latest addition to our line of Spectroscopic Ellipsometers", printed from www.jawoolam.com on Nov. 5, 2002.
Request for Ex Parte Reexamination for US Patent # 7,067,818 filed Feb. 11, 2009.
Request for Ex Parte Reexamination for US Patent # 7,067,818 filed Feb. 12, 2010.
Request for Ex Parte Reexamination for US Patent # 7,026,626 filed Nov. 7, 2008.
U.S. Appl. No. 12/590,151 Official Action dated Jun. 25, 2010.
U.S. Appl. No. 12/834,939 "Combined optical metrology techniques" filed on Jul. 13, 2010.
Lalanne, P., "Improved Formulation of the Coupled-Wave Method for Two-Dimensional Gratings", Optical Society of America, vol. 14, No. 7. Jul. 1997, pp. 1592-1598.
Lalanne, P., "On the Effective Medium Theory of Subwavelength Periodic Structures", Journal of Modern Optics, vol. 43, No. 10, pp. 2063-2085, year 1996.
Kinber et al., "Use of Symmetry in Solving Diffraction Problems", Radio Engineering and Electronic Physics, vol. 16, pp. 581-587, year 1971.
Moharam et al.., "Stable Implementation of the Rigorous Coupled-Wave Analysis for Surface-Relief Gratings: Enhanced Transmittance Matrix Approach", Optical Society of America, vol. 12, No. 5, pp. 1077-1086, May 1995.
Moharam et al., "Formulation for Stable and Efficient Implementation of the Rigorous Coupled-Wave Analysis of Binary Gratings", Optical Sooety of America, vol. 12, No. 5, pp. 1068-1076, May 1995.
Li, L., "Using Symmetries of Grating Groove Profiles to Reduce Computation Cost of the C Method", Optical Society of America, vol. 24, No. 4, pp. 1085-1096, Apr. 2007.
JP Patent Application # 528098/06 Official Action dated Aug. 30, 2011.
U.S. Appl. No. 12/854,917 Official Action dated Jul. 28, 2011.
U.S. Appl. No. 12/454,837 Official Action dated Oct. 3, 2011.
U.S. Appl. No. 12/876,242 Official Action dated Nov. 19, 2010.

* cited by examiner

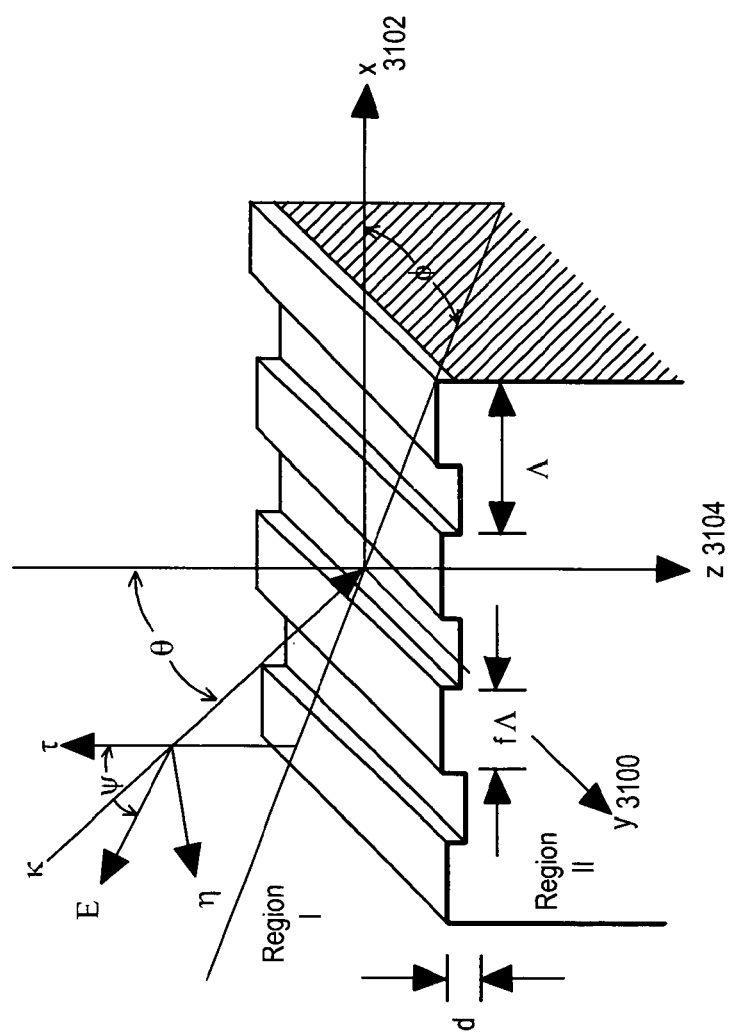
FIG. 3 - (Prior Art)

METHOD AND SYSTEM FOR USING REFLECTOMETRY BELOW DEEP ULTRA-VIOLET (DUV) WAVELENGTHS FOR MEASURING PROPERTIES OF DIFFRACTING OR SCATTERING STRUCTURES ON SUBSTRATE WORK PIECES

CROSS-REFERENCE TO RELATED APPLICATION

This application is a continuation-in-part of U.S. patent application Ser. No. 12/080,947, filed Apr. 7, 2008, which claims priority to U.S. Provisional Patent Application No. 60/922,434, filed Apr. 9, 2007. This application is also a continuation-in-part of U.S. patent application Ser. No. 12/590,151, filed Nov. 3, 2009, which is a continuation of U.S. patent application Ser. No. 12/231,350, filed Sep. 2, 2008 (now abandoned), which is a continuation of U.S. patent application Ser. No. 11/517,894, filed Sep. 8, 2006 (now U.S. Pat. No. 7,446,876), which is a continuation of U.S. patent application Ser. No. 10/909,126, filed Jul. 30, 2004 (now U.S. Pat. No. 7,126,131), which is a continuation-in-part of U.S. patent application Ser. No. 10/668,642 filed Sep. 23, 2003 (now U.S. Pat. No. 7,067,818), which claims priority to U.S. Provisional Patent Applications No. 60/440,434, 60/440,435, and 60/440,443 all filed Jan. 16, 2003. All the applications cited above are incorporated herein by reference.

TECHNICAL FIELD OF THE INVENTION

This disclosure relates to a method for using single-wavelength, multiple-wavelength, or broadband reflectometry that include below deep ultra-violet (DUV) wavelengths for measuring properties of diffracting and/or scattering structures on substrate work-pieces, such as, for example, semiconductor substrates.

BACKGROUND

Optical methods for control of critical dimensions and/or profile of etched and lithographic structures in high-volume semiconductor manufacturing environments are gaining wide acceptance, largely due to the promise of rapid, nondestructive real-time feedback for cost-effective process control.

Among the earliest current art metrology systems are scatterometry systems, such as the method taught in U.S. Pat. Nos. 5,164,790 or 5,703,692, which determine angle-resolved spectral response from periodic structures. Later current art metrology systems employed traditional thin film analysis tools, such as broad-band reflectometers and ellipsometers, as taught in U.S. Pat. Nos. 5,432,607, 6,281,674, or 6,898,537.

Most of the various current designs operate in a spectral region between deep ultraviolet (DUV) (~200 nm) and near infra-red (~1000 nm) wavelengths. This limits the fundamental resolution of such systems when measuring structures much smaller than the incident wavelength, and causes the metrology to lose sensitivity to the details of profile shape. As such, current optical metrology becomes increasingly obsolete as semiconductor device dimensions shrink.

At a given wavelength range, the more incident conditions an optical tool measures, the greater the sensitivity of the measurement to a greater number of parameters. Accordingly, some recent current art systems overcome some of the resolution issue by combining ellipsometric and polarimetric (polarized reflectance) data, such as the methods taught in U.S. Pat. Nos. 6,713,753 and 6,590,656, at the expense of greater complexity and less versatility in a manufacturing environment. Another approach combines broadband reflectance, polarimetric, or ellipsometric data with multiple angle of incidence measurements, such as the method taught in the article T. Novikova, A. Martino, S. B. Hatit, and B. Drevillon, "Application of Mueller polarimetry in conical diffraction for critical dimension measurements in microelectronics", Appl. Opt., Vol. 45, No. 16, p. 2006. Such systems are complicated to operate, often slow, and are very hard to integrate into the manufacturing process. Aside from this, there is still the fundamental issue that resolution information is lost as the measured feature sizes decrease, and after a certain point, no amount of additional datasets will compensate for this.

On another front, optical data from metrology tools are often analyzed using rigorous solutions to the boundary value problem. One of the most common analysis technique for periodic structures is the rigorous coupled wave (RCW) method, which is sometimes also referred to as the Fourier Modal method. The RCW method is used to compute theoretical optical spectra representative of the structure being measured as the model parameters are changed during a regression analysis. The optimized parameters are the measurement result.

The RCW calculation can be very computationally intensive. In some cases, a library database is used to store pre-generated spectra to be compared with the measured spectra during measurement. Even then, the efficiency of the calculation is important since hundreds of thousands or even millions of spectra can be required for the database.

The special case of normal incidence benefits from symmetry conditions at all wavelength ranges, allowing for the most efficient RCW calculations. In addition, a normal incidence reflectometer is more suited to integration into the device manufacturing process, being less complicated to operate, easier to maintain, and more compact than the angle-resolved or ellipsometric solutions mentioned above.

Thus, it is desirable to have a reflectometer configured for normal incidence measurement for practical reasons, but also capable of using below deep ultra-violet (DUV) wavelength light for enhanced measurement capabilities. Instances of normal incidence polarized reflectometry in the current art, such as the one disclosed in U.S. Pat. No. 6,898,537, are not suitable for operation below DUV. The patent teaches a calibration method to account for the offset between different polarization conditions, which will not work in the region below DUV due to contaminant buildup during the tool's operation. In general, it is quite difficult to polarize light below ~160 nm. In addition, the calibration of the absolute reflectance used by the system disclosed in U.S. Pat. No. 6,898,537 is complicated by the lack of reliable reflectance reference standards in the range below DUV. Therefore, the method disclosed in U.S. Pat. No. 6,898,537 is unsuitable for work below DUV wavelength range. A further complication arises in the use of polarized reflectance with an r-θ stage, and an elaborate polarization alignment procedure is required during measurement of periodic structures, since the orientation of the structures will vary as a function of r-θ position.

SUMMARY OF THE INVENTION

The techniques disclosed herein measure broadband below deep ultra-violet DUV-Visible (Vis) or near infra-red (NIR) reflectance spectra from diffracting and scattering features.

One technique of the system uses a wavelength range of 120 nm-800 nm. The wide wavelength range provides a large set of incident conditions for improved sensitivity to multiple parameters, negating the need for complicated arrangements to impose multiple angle and polarization conditions. In addition, the inclusion of the portion of the spectrum below DUV enhances sensitivity to smaller feature sizes. The techniques disclosed herein also use an r-θ stage together with un-polarized normal incidence reflectance so that a smaller footprint is retained without the need for complicated polarization alignment. In addition, a faster calculation speed can be achieved for periodic structures by exploiting the natural symmetry of the diffraction calculation in a normal incident condition.

The present disclosure provides a method of optically measuring diffracting and scattering structures on a sample, comprising providing a below deep ultra-violet (DUV)-Vis referencing reflectometer, wherein referencing is used to account for system and environmental changes to adjust reflectance data obtained through use of the reflectometer, providing at least one computer, and extracting structural and optical parameters from a theoretical model of the diffracting and scattering structure via a computer.

In one embodiment, the referencing reflectometer is configured for normal incidence, allowing for use of a reduced RCW calculation when analyzing 2-D periodic structures, or use of a group theoretic approach when analyzing 3-D periodic structures, to take advantage of the symmetry. It should be pointed out that while a reduced RCW calculation is advantageous, its use is not required. Use of the full RCW calculation as well as analysis methods other than RCW, which may or may not make use of symmetry, is not precluded. The system can also be used to measure non-symmetric periodic structures (using, e.g. the full RCW or other rigorous method) as well as non-periodic structures, employing any number of methods available in the literature, either rigorous or approximate. The incident light can be un-polarized.

In one embodiment, a reflectometer apparatus for analyzing a scattering or diffracting structure is provided. The reflectometer may comprise a below deep ultra-violet (DUV) wavelength referencing reflectometer configured for normal incidence operation and having a light source that provides at least below DUV wavelength light, wherein referencing is configured to account for system and environmental changes to adjust reflectance data obtained through use of the reflectometer. The reflectometer may also comprise at least one computer connected to the reflectometer and a computer program for use with the at least one computer configured to extract structural and optical parameters from a theoretical model of the scattering or diffracting structure. The computer program uses a reduced RCW calculation for analyzing 2-D periodic structures of the scattering or diffracting structure.

In one embodiment, a method of optically measuring diffracting and scattering features on a sample is disclosed. The method may comprise providing an optical signal having at least some below deep ultraviolet light wavelengths and directing the light on the sample in a substantially normally incident configuration, wherein the incident light is un-polarized. The method may further comprise utilizing a reduced RCW calculation to analyze 2-D periodic structures and utilizing a group theoretic approach to analyze 3-D periodic structures.

In another embodiment a method of optically measuring diffracting and scattering features on a sample is disclosed. The method may comprise providing a reflectometer that utilizes at least some below deep ultra-violet wavelengths of light and measuring intensity data from a plurality of sites within an area of the sample. The method may further comprise analyzing a combination of the measured intensity data from the plurality of sites that is independent of incident intensity in order to extract structural and/or optical property information regarding the sample.

In another embodiment a method of optically measuring diffracting and scattering features on a sample is disclosed. The method may comprise providing a reflectometer that utilizes at least some below deep ultra-violet wavelengths of light and measuring intensity data from a plurality of sites within an area of the sample. At least one of the sites represents an un-patterned region of the sample and at least one other site represents a patterned region of the sample.

In another embodiment, a method for measuring properties of a sample is disclosed. The method comprises providing an optical metrology tool that includes a first optical metrology apparatus, the first optical metrology apparatus being a first reflectometer having at least in part below deep ultra-violet light wavelengths, and providing a second optical metrology apparatus within the optical metrology tool, the second optical metrology apparatus providing optical measurements for the sample utilizing a different optical metrology technique as compared to the first optical metrology apparatus. Data sets from the first optical metrology apparatus and the second optical metrology apparatus are combined and analyzed in order to measure at least one property of the sample.

In another embodiment a reflectometer apparatus for analyzing a scattering or diffracting structure is disclosed. The apparatus may comprise a below deep ultra-violet (DUV) wavelength referencing reflectometer configured for normal incidence operation and having an unpolarized light source and non-polarizing optical system that provides at least below deep ultra-violet wavelength light, wherein referencing is configured to account for system and environmental changes to adjust reflectance data obtained through use of the reflectometer. The apparatus may further comprise at least one computer connected to the reflectometer, and a computer program for use with the at least one computer configured to extract structural and optical parameters from a theoretical model of the scattering or diffracting structure. The apparatus may further comprise an r-θ stage for holding the scattering or diffracting structure, wherein a calculated reflectance is obtained from a relationship that is independent of a sample rotation.

As described below, other features and variations can be implemented, if desired, and a related method can be utilized, as well.

DESCRIPTION OF THE DRAWINGS

It is noted that the appended drawings illustrate only exemplary embodiments of the invention and are, therefore, not to be considered limiting of its scope, for the invention may admit to other equally effective embodiments.

FIG. 3 is schematic illustrating polar (theta) and azimuth (phi) incident angles.

DETAILED DESCRIPTION OF THE INVENTION

Figure 1:
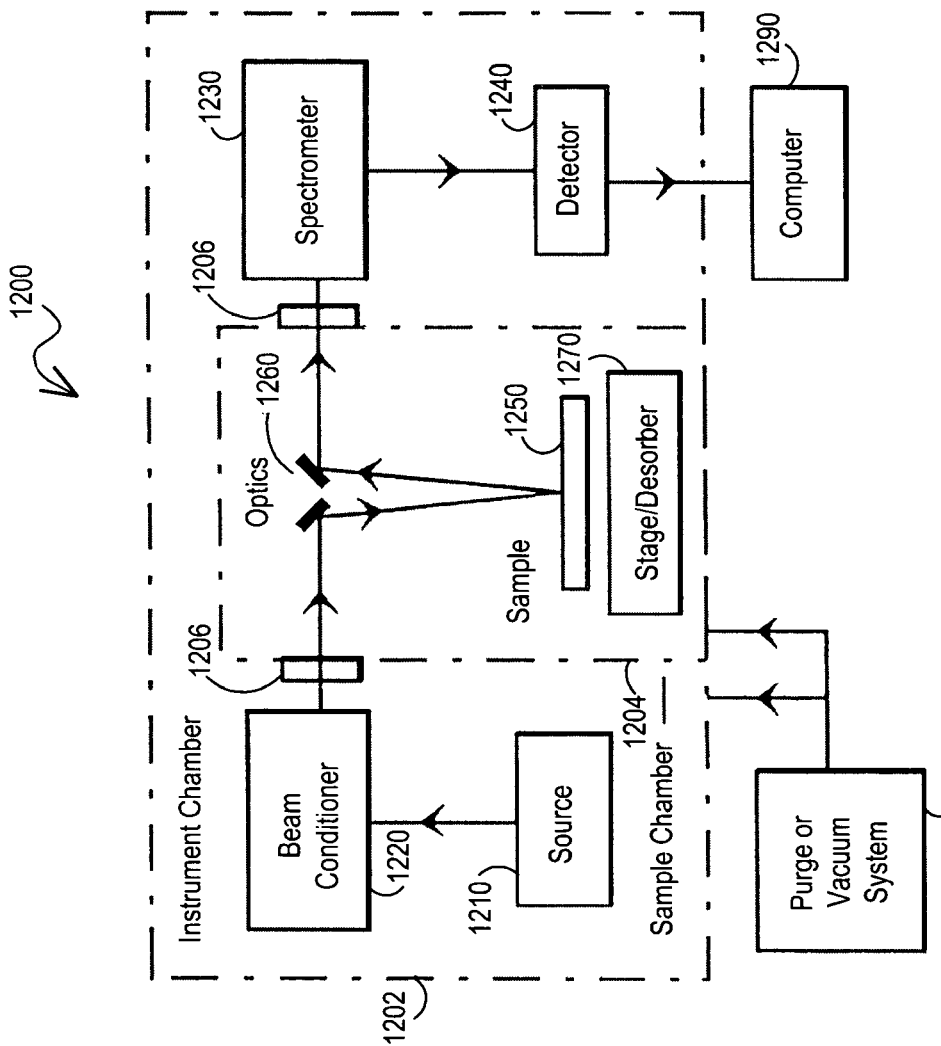
FIG. 1 is a schematic representation of a reflectometer.

The techniques disclosed herein involve an extension of the recent technology taught in U.S. Pat. No. 7,067,818 titled "Vacuum Ultraviolet Reflectometer System and Method", U.S. Pat. No. 7,026,626 titled "Semiconductor Processing Techniques Utilizing Vacuum Ultraviolet Reflectometer", and U.S. Pat. No. 7,126,131 titled "Broad Band Referencing Reflectometer", which are all expressly incorporated in their entirety herein by reference. One technique measures reflectance spectrum in the 120 nm-800 nm wavelength range, providing a much greater spectral range than any existing reflectometer. Preferred techniques disclosed herein operate at normal incidence partly to minimize the overall footprint. Another technique additionally uses an r-θ stage, further reducing the footprint of the sample area.

To enhance the sensitivity of optical metrology equipment for challenging applications it is desirable to extend the range of wavelengths over which such measurements are performed. Specifically, it is advantageous to utilize shorter wavelength (higher energy) photons extending into, and beyond, the region of the electromagnetic spectrum referred to as the vacuum ultra-violet (VUV). Historically there has been relatively little effort expended on the development of optical instrumentation designed to operate at these wavelengths, owing to the fact that VUV (and lower) photons are strongly absorbed in standard atmospheric conditions. Vacuum ultra-violet (VUV) wavelengths are generally considered to be wavelengths less than deep ultra-violet (DUV) wavelengths. Thus VUV wavelengths are generally considered to be wavelengths less than about 190 nm. While there is no universal cutoff for the bottom end of the VUV range, some in the field may consider VUV to terminate and an extreme ultra-violet (EUV) range to begin (for example some may define wavelengths less than 100 nm as EUV). Though the principles described herein may be applicable to wavelengths above 100 nm, such principles are generally also applicable to wavelengths below 100 nm. Thus, as used herein it will be recognized that the term VUV is meant to indicate wavelengths generally less than about 190 nm however VUV is not meant to exclude lower wavelengths. Thus as described herein VUV is generally meant to encompass wavelengths generally less than about 190 nm without a low end wavelength exclusion. Furthermore, low end VUV may be construed generally as wavelengths below about 140 nm.

Indeed it is generally true that virtually all forms of matter (solids, liquids and gases) exhibit increasingly strong optical absorption characteristics at VUV wavelengths. Ironically it is this same rather fundamental property of matter which is partly (along with decreased wavelength versus feature size) responsible for the increased sensitivity available to VUV optical metrology techniques. This follows as small changes in process conditions, producing undetectable changes in the optical behavior of materials at longer wavelengths, can induce substantial and easily detectable changes in the measurable characteristics of such materials at VUV wavelengths.

The fact that VUV photons are strongly absorbed by most forms of matter precludes the simple extension of, or modification to, conventional longer wavelength optical metrology equipment in order to facilitate operation in the VUV. Current day tools are designed to operate under standard atmospheric conditions and typically lack, among other things, the controlled environment required for operation at these shorter wavelengths. VUV radiation is strongly absorbed by both $O_2$ and $H_2O$ molecules and hence these species must be maintained at sufficiently low levels as to permit transmission of VUV photons through the optical path of the instrument. The transmission of photons through standard atmosphere drops precipitously at wavelengths shorter than about 200 nm.

Not only are conventional optical instruments intended to function in standard atmospheric conditions, they also typically employ an array of optical elements and designs which render them unsuitable for VUV operation. In order to achieve highly repeatable results with a reflectometer it is desirable to provide a means by which reflectance data can be referenced or compared to a relative standard. In this manner changes in the system that occur between an initial time when the system is first calibrated and a later time when a sample measurement is performed, can be properly accounted for. At longer wavelengths such changes are usually dominated by intensity variations in the spectral output of the source. When working at VUV wavelengths, however, changes in the environmental conditions (i.e. changes in the concentration of absorbing species in the environment of the optical path) can play a much larger role.

Thus, conventional longer wavelength systems fail to address the significant influence that the absorbing environment has on the measurement process. To ensure that accurate and repeatable reflectance data is obtained, it is desirable to not only provide a means of controlling the environment containing the optical path, but furthermore to ensure that the absorption effects which do occur are properly taken into account during all aspects of the calibration, measurement and reference processes.

Hence, it is desirable to provide an optical metrology tool with a controlled environment that is designed to operate at and below VUV wavelengths. In addition, in order to ensure that accurate and repeatable results are obtained, it is desirable that the design incorporate a robust referencing methodology that acts to reduce or altogether remove errors introduced by changes in the controlled environment.

Examples of a VUV optical metrology instrument well suited to benefit from use of the methods herein described are disclosed in the above-mentioned U.S. application Ser. No. 10/668,642, filed on Sep. 23, 2003, now U.S. Pat. No. 7,067,818; U.S. application Ser. No. 10/909,126, filed on Jul. 30, 2004, now U.S. Pat. No. 7,126,131; and U.S. application Ser. No. 11/600,413, filed on Nov. 16, 2006 now U.S. Pat. No. 7,342,235, the disclosures of which are all expressly incorporated in their entirety herein by reference. The metrology instrument may be a broad-band reflectometer specifically designed to operate over a broad range of wavelengths, including the VUV. A schematic representation of an optical reflectometer metrology tool 1200 that depicts one technique disclosed herein is presented in FIG. 1. As is evident, the source 1210, beam conditioning module 1220, optics (not shown), spectrometer 1230 and detector 1240 are contained within an environmentally controlled instrument (or optics) chamber 1202. The sample 1250, additional optics 1260, motorized stage/sample chuck 1270 (with optional integrated desorber capabilities) and sample are housed in a separate environmentally controlled sample chamber 1204 so as to enable the loading and unloading of samples without contaminating the quality of the instrument chamber environment. The instrument and sample chambers are connected via a controllable coupling mechanism 1206 which can permit the transfer of photons, and if so desired the exchange of gases to occur. A purge and/or vacuum system 1280 may be coupled to the instrument chamber 1202 and the sample chamber 1204 such that environmental control may be exercised in each chamber.

Additionally a computer 1290 located outside the controlled environment may be used to analyze the measured data. A computer program for extracting structural and optical parameters from a theoretical model of the diffracting and scattering structure is included in the computer 1290. The referencing reflectometer is configured for normal incidence. A reduced RCW calculation can be used for analyzing 2-D periodic structures to take advantage of the symmetry. Similarly, a group theoretic approach can be used for analyzing 3-D periodic structures to take advantage of the symmetry. The incident light can be un-polarized. It will be recognized that computer 1290 may be any of a wide variety of computing or processing means that may provide suitable data processing and/or storage of the data collected.

While not explicitly shown in FIG. 1, it is noted that the system could also be equipped with a robot and other associated mechanized components to aid in the loading and unloading of samples in an automated fashion, thereby further increasing measurement throughput. Further, as is known in the art load lock chambers may also be utilized in conjunction with the sample chamber to improve environmental control and increase the system throughput for interchanging samples.

In operation light from the source 1210 is modified, by way of beam conditioning module 1220, and directed via delivery optics through the coupling mechanism windows 1206 and into the sample chamber 1204, where it is focused onto the sample by focusing optics 1260. Light reflected from the sample is collected by the focusing optics 1260 and re-directed out through the coupling mechanism 1206 where it is dispersed by the spectrometer 1230 and recorded by a detector 1240. The entire optical path of the device is maintained within controlled environments which function to remove absorbing species and permit transmission of below DUV photons.

Referring again to FIG. 1, the beam conditioner module 1220 allows for the introduction of spatial and/or spectral filtering elements to modify the properties of the source beam. While this functionality may not generally be required, there may arise specific applications where it is deemed advantageous. Examples could include modifying the spatial or temporal coherence of the source beam through use of an aperture, or introduction of a "solar blind" filter to prevent longer wavelength light from generating spurious below DUV signals through scattering mechanisms that may occur at the various optical surfaces in the optical beam path.

The beam conditioner can also include a polarizer, which would be useful for critical dimension measurements where it is desirable to polarize the incident light in a particular direction with respect to the measured structures. Alternately, it may be desirable to have a non-polarizing optical path, and the beam conditioner can consist of a depolarizer to counter the effects of any polarization imparted by the preceding optics. Additionally, either a polarizing or depolarizing beam conditioner can be placed in the optical path on the detection side of the sample. A depolarizer at this location would be useful for eliminating any polarization effects of the detection system.

While in some techniques disclosed herein the reflectance data can be polarized in particular directions with respect to a diffracting structure, one technique uses an un-polarized broadband source. This is partly advantageous due to the difficulty in polarizing below deep ultra-violet (DUV) light, but also allows a more straight-forward use of an r-θ stage, since the normal incidence un-polarized spectrum is the same regardless of sample orientation. This technique is advantageous in high volume manufacturing environments, and in particular is well-suited to integrated applications.

These advantages are retained without giving up measurement capability of the system. The below DUV portion of the spectra is potentially much richer than DUV-visible (DUV-Vis) light, for both scattering and non-scattering structures, for two primary reasons: 1) the wavelength vs. feature size is much smaller than with conventional DUV-Vis optical metrology, and 2) many materials that have relatively featureless dispersions in the DUV-Vis range have very rich absorption spectra in the below DUV range, which leads to a stronger response of the spectra at these wavelengths. In combination, the inclusion of the below DUV spectrum can easily make up for or exceed the additional spectral information contained in conventional DUV-Vis multiple angle ellipsometric configurations.

An additional difficulty in using below DUV spectrometry is caused by a contaminant buildup that occurs on optical components and reference samples due to the interaction of common fab materials with high energy radiation. This contaminant buildup has particular relevance to absolute reflectance calibration, since it is difficult to maintain a consistent reference sample. Accordingly, one technique disclosed herein incorporates new calibration procedures as described in U.S. application Ser. No. 10/930,339, filed on Aug. 31, 2004, and also described in U.S. application Ser. No. 11/418,827, filed on May 5, 2006, now U.S. Pat. No. 7,282,703, and U.S. application Ser. No. 11/418,846, filed on May 5, 2006, all of which are incorporated herein in their entirety by reference.

Figure 2:
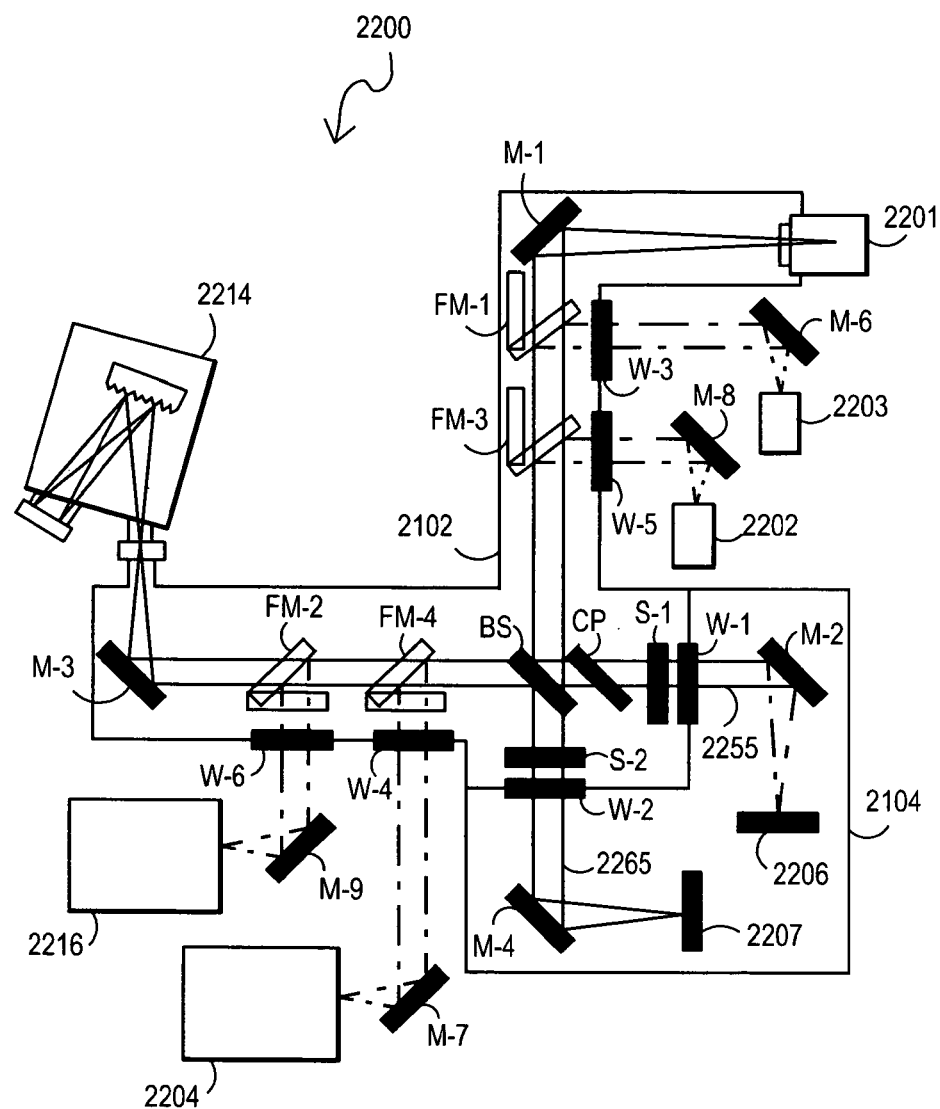
FIG. 2 is a more detailed schematic representation of a reflectometer.

A more detailed schematic of the optical aspects of the instrument is presented in FIG. 2. The instrument is configured to collect referenced broad band reflectance data in the below DUV and two additional spectral regions. In operation light from these three spectral regions may be obtained in either a parallel or serial manner When operated in a serial fashion reflectance data from the below DUV is first obtained and referenced, following which, reflectance data from the second and then third regions is collected and referenced. Once all three data sets are recorded they are spliced together to form a single broad band spectrum. In parallel operation reflectance data from all three regions are collected, referenced and recorded simultaneously prior to data splicing.

The instrument is separated into two environmentally controlled chambers, the instrument chamber 2102 and the sample chamber 2104. The instrument chamber 2102 houses most of the system optics and is not exposed to the atmosphere on a regular basis. The sample chamber 2104 houses the sample and reference optics, and is opened regularly to facilitate changing samples. For example, the instrument chamber 2102 may include mirrors M-1, M-2, M-3, and M-4. Flip-in mirrors FM-1 and FM-3 may be utilized to selective chose which light source 2201, 2202 and 2203 is utilized (each having a different spectral region). Flip-in mirrors FM-2 and FM-4 may be utilized to selective chose one of spectrometers 2204, 2216, and 2214 (again depending upon the chosen spectral region). As mentioned above with reference to FIG. 1, the spectrometers may be any of a wide variety of types of spectrometers. Mirrors M-6, M-7, M-8 and M-9 may be utilized to help direct the light beams as shown. Windows W-1 and W-2 couple light between the instrument chamber 2102 and sample chamber 2104. Windows W-3, W-4, W-5 and W-6 couple light into and out of the instrument chamber 2102. Beam splitter BS and shutters S-1 and S-2 are utilized to selectively direct light to a sample 2206 or a reference 2207 with the assistance of mirrors M-2 and M-4 as shown (the reference may be a mirror in one embodiment). The sample beam passes through compensator plate CP. The compensator plate CP is included to eliminate the phase difference that would occur between the sample and reference paths resulting from the fact that light traveling in the sample channel passes through the beam splitter substrate but once, while light traveling in the reference channel passes through the beam splitter substrate three times due to the nature of operation of a beam splitter. Hence, the compensator plate may be constructed of the same material and is of the same thickness as the beam splitter. This ensures that light traveling through the sample channel also passes through the same total thickness of beam splitter substrate material.

When operated in a serial fashion below DUV data is first obtained by switching the second spectral region flip-in source mirror FM-1 and third spectral region flip-in source mirror FM-2 into the "out" position so as to allow light from the below DUV source to be collected, collimated and redirected towards beam splitter element BS by the focusing mirror M-1. Light striking the beam splitter is divided into two components, the sample beam 2255 and the reference beam 2265, using a near-balanced Michelson interferometer arrangement. The sample beam is reflected from the beam splitter BS and travels through the compensator plate CP, sample shutter S-1 and sample window W-1 into the sample chamber 2104, where it is redirected and focused onto the sample 2206 via a focusing mirror M-2. The reference shutter S-2 is closed during this time. The sample window W-1 is constructed of a material that is sufficiently transparent to below DUV wavelengths so as to maintain high optical throughput.

Light reflected from the sample is collected, collimated and redirected by the sample mirror M-2 back through the sample window, where it passes through the sample shutter and compensator plate. The light then continues on unhampered by the first spectral region flip-in detector mirror FM-2 and the second spectral region flip-in detector mirror FM-4 (switched to the "out" position), where it is redirected and focused onto the entrance slit of the below DUV spectrometer 2214 by the focusing mirror M-3. At this point light from the sample beam is dispersed by the VUV spectrometer and recorded by its associated detector. The spectrometer may be any of a wide variety of spectrometers including those types disclosed in U.S. application Ser. No. 11,711,482, filed on Feb. 27, 2007, the disclosure of which is incorporated in its entirety herein. Thus, the spectrometer configuration is not intended to be limited to the particular configuration shown in the figure.

Following collection of the sample beam, the reference beam is measured. This is accomplished by closing the sample shutter S-1 and opening the reference shutter S-2. This enables the reference beam to travel through the beam splitter BS, reference shutter S-2 and reference window W-2 into the sample chamber 2104, wherein it is redirected and focused by mirror M-4 onto the plane reference mirror 2207 which serves as the reference. The reference window is also constructed of a material that is sufficiently transparent to VUV wavelengths so as to maintain high optical throughput.

Light reflected from the surface of the plane reference mirror 2207 travels back towards the focusing reference mirror M-4 where it is collected, collimated and redirected through the reference window W-2 and the reference shutter S-2 towards the beam splitter BS. Light is then reflected by the beam splitter towards the focusing mirror M-3 where it is redirected and focused onto the entrance slit of the VUV spectrometer 2214. The path length of the reference beam 2265 is specifically designed so as to match that of the sample beam 2255 in each of the environmentally controlled chambers.

Following measurement of the below DUV data set, the second spectral region data set is obtained in a similar manner During collection of the second region spectral data both the second spectral region source flip-in mirror FM-1 and the second spectral region detector flip-in mirror FM-2 are switched to the "in" position. As a result, light from the below DUV source 2201 is blocked and light from the second spectral region source 2203 is allowed to pass through window W-3, after it is collected, collimated and redirected by its focusing mirror M-6. Similarly, switching the second spectral region detector flip-in mirror FM-2 into the "in" position directs light from the sample beam (when the sample shutter is open and the reference shutter is closed) and reference beam (when the reference shutter is open and the sample shutter is closed) through the associated window W-6 and onto the mirror M-9 which focuses the light onto the entrance slit of the second spectral region spectrometer 2216, where it is dispersed and collected by its detector.

Data from the third spectral region is collected in a similar fashion by flipping "in" the third spectral region source flip-in mirror FM-3 and the third spectral region detector flip-in mirror FM-4, while flipping "out" the second spectral region source flip-in mirror FM-1 and the second spectral region detector flip-in mirror FM-2.

Once the sample and reference measurements for each of the spectral regions have been performed, a computer or processor (not shown) can be used to calculate the referenced reflectance spectra in each of the three regions. Finally, these individual reflectance spectra are combined to generate a single reflectance spectrum encompassing the three spectral regions.

When operated in a parallel mode, the source and detector flip-in mirrors are replaced with appropriate beam splitters so that data from all three spectral regions are recorded simultaneously.

Again, a polarizer can be included in the incident optical path before the beam splitter in order to polarize the incident light in a particular direction with respect to the measured structures. Alternately, it may be desirable to have a non-polarizing optical path, and a non-polarizing beam splitter can be used in conjunction with an unpolarized source. If necessary, a depolarizer can be included in the optical path just before the beam splitter to counter the effects of any polarization imparted by the preceding optics. Additionally, either a polarizing or depolarizing beam conditioner can be placed in the optical path on the detection side of the sample, after the beam splitter. A depolarizer at this location would be useful for eliminating any polarization effects of the detection system.

The spectral information is generally analyzed using regression or library techniques. The techniques disclosed herein may take advantage of the symmetry of the normal incidence configuration by reformulating the RCW eigen-problem for the normal incidence case. For two dimensional periodic structures, a method distinct from that taught in U.S. Pat. No. 6,898,537 is described here, in that the current method uses a more general derivation that leads to a different eigen-problem formulation, is more efficient in its treatment of the TM case, and does not require modification of the form of the boundary problem. For three dimensional structures, such as contact holes or vias, the formulation disclosed in the techniques described herein for 2-D structures can be generalized. Alternately the methods in Benfeng Bai and Lifeng Li, "Reduction of computation time for crossed-grating problems: a group theoretic approach," J. Opt. Soc. Am. A 21, 1886-1894 (2004), and subsequent publications can be employed to take advantage of the normal incidence configuration for 3-D periodic structures.

The steps leading to the reduced RCW computation for 2-D structures are now described. The description follows the treatment and notation described in M. G. Moharam, E. B. Grann, D. A. Pommet, and T. K. Gaylord, "Formulation for stable and efficient implementation of the rigorous coupled-wave analysis of binary gratings," J. Opt. Soc. Am. A 12, 1068-1076 (1995) and illustrated in FIG. 3. Note that unreduced eigen-problem matrix and vector indices run from −N to N, with the (−N, −N) matrix element at the top left corner, in order to be consistent with a symmetric diffraction problem with positive and negative orders. When creating a computer algorithm, we will need to label the indices from 1 to 2N+1, or 0 to 2N, depending on the programming language used. Obviously, this is a notation preference and has no effect on the outcome. The indices of the reduced matrices will run from 0 to N in either case.

FIG. 3 illustrates the geometry of the problem. We first note that it is possible to decouple two independent incident polarizations—TE and TM, as long as the plane of incidence is in the phi=0 configuration. That is, the plane of incidence is perpendicular to the grating lines. An arbitrary polarization can be expressed as a linear combination of the TE and TM cases. In particular, for an un-polarized incident beam, which will include equal components of all possible polarizations, one can take the average over all of the polarization conditions to obtain $$R = \frac{1}{2}(R_{TE} + R_{TM}), \quad \text{eq. 1}$$

where R is the specular zero-order reflectance. This means that the reflectance can be computed for un-polarized incident light by computing the TE and TM reflectances separately, and then taking the average. The advantage to doing this is that with the normal incidence condition, the grating orientation is immaterial—the reflectance from the grating can always be obtained from eq. 1 for un-polarized incident light.

First, the conventional formulation for the TE case must be described. In this case, the electric field has only a y-component 3100 (parallel to the grating lines), while the magnetic field H has both x- 3102 and z-components 3104, but no y-component. The fields in each of the 3 regions shown in FIG. 3 are expanded as generalized Fourier series:

$$E_{inc,y} = \exp[-jk_0 n_I(\sin\theta x + \cos\theta z)], \quad \text{eq. 2}$$

$$E_{I,y} = E_{inc,y} + \sum_{i=-\infty}^{\infty} R_i \exp[-j(k_{xi} - k_{I,zi}z)] \quad \text{eq. 3}$$

in the incident region ($k_0 = 2\pi/\lambda$), $$E_{II,y} = \sum_{i=-\infty}^{\infty} T_i \exp\{-j[k_{xi}x + k_{II,zi}(z-d)]\}, \quad \text{eq. 4}$$

in the substrate medium, and $$E_{gy} = \sum_{i=-\infty}^{\infty} S_{yi}(z)\exp(-jk_{xi}x), \quad \text{eq. 5}$$

$$H_{gx} = -j\left(\frac{\varepsilon_f}{\mu_f}\right)^{1/2} \sum_{i=-\infty}^{\infty} U_{xi}(z)\exp(-jk_{xi}x) \quad \text{eq. 6}$$

for the tangential fields in the grating region, where $$k_{xi} = k_0[n_I\sin\theta - i(\lambda_0/\Lambda)], \quad \text{eq. 7}$$

and $$k_{l,zi} = \begin{cases} k_0[n_l^2 - (k_{xi}/k_0)^2]^{1/2} & k_0 n_l > k_{xi} \\ -jk_0[(k_{xi}/k_0) - n_l^2]^{1/2} & k_{xi} > k_0 n_l, \end{cases} \quad l = I, II \quad \text{eq. 8}$$

$\varepsilon_f$ is the permittivity of free space, and $\mu_f$ is the magnetic permeability of free space. The permittivity in the grating region is also expanded as a Fourier series:

$$\varepsilon(x) = \sum_h \varepsilon_h \exp\left(j\frac{2\pi h}{\Lambda}\right), \quad \text{eq. 9}$$

$$\varepsilon_0 = n_{rd}^2 f + n_{gr}^2 (1-f),$$

$$\varepsilon_h = (n_{rd}^2 - n_{gr}^2)\frac{\sin(\pi h f)}{\pi h},$$

where $n_{rd}$ is the complex index of refraction of the grating ridges, and $n_{gr}$ is the complex index of refraction of the grating groves.

The fields everywhere satisfy the Maxwell equation:

$$\vec{H} = \left(\frac{j}{\omega\mu}\right)\nabla \times \vec{E}, \quad \text{eq 10}$$

where $\omega$ is the angular frequency, and $\mu$ is the magnetic permeability. Usually, we assume $\mu = \mu_f$.

In the grating region, eq. 10 gives $$\frac{\partial E_{gy}}{\partial z} = j\omega\mu_f H_{gx}, \quad \text{eq. 11}$$

$$\frac{\partial H_{gx}}{\partial z} = j\omega\varepsilon_f \varepsilon(x) E_{gy} + \frac{\partial H_{gz}}{\partial x} \quad \text{eq. 12}$$

Substituting eqs. 5 and 6 into eqs. 11 and 12 leads to $$\frac{\partial S_{yi}}{\partial z} = k_0 U_{xi}, \quad \text{eq. 13}$$

$$\frac{\partial U_{xi}}{\partial z} = \left(\frac{k_{xi}^2}{k_0}\right)S_{yi} - k_0 \sum_{p=-\infty}^{\infty} \varepsilon_{(i-p)} S_{yp}, \quad \text{eq. 14}$$

which are the set of coupled equations to be solved for the spatial harmonic components of the fields, $S_{yi}$ and $U_{xi}$.

When put in matrix form, eqs. 13 and 14 are $$\begin{bmatrix} \frac{\partial S_y}{\partial(z')} \\ \frac{\partial U_x}{\partial(z')} \end{bmatrix} = \begin{bmatrix} 0 & I \\ A & 0 \end{bmatrix} \begin{bmatrix} S_y \\ U_x \end{bmatrix} \quad \text{eq. 15}$$

where $z' = k_0 z$. In eq. 15, $$A = K_x^2 - E, \quad \text{eq. 16}$$

$K_x$ is a diagonal matrix with elements $k_{xi}/k_0$, and E is the permittivity matrix, whose elements consist of the permittivity harmonic components:

$$E_{i,j} = \varepsilon_{(i-j)}. \quad \text{eq. 17}$$

The permittivity matrix, E, should not be confused with the electric field, which will always have a Cartesian component subscript.

Equation 15 can be further reduced to $$\left[\frac{\partial^2 S_y}{\partial (z')^2}\right] = [A][S_y]. \qquad \text{eq. 18}$$

Eq. 18 is in practice truncated after order N, which corresponds to retaining 2N+1 spatial harmonic terms in all of the Fourier series (positive and negative orders plus the zero term), leaving 2N+1 column vectors for $S_y$ and $$\left[\frac{\partial^2 S_y}{\partial (z')^2}\right],$$

and a (2N+1)×(2N+1) matrix A.

The general solution for eq. 18, for a given truncation order N, can be expressed in terms of the eigenvalues and eigenvectors of the matrix A:

$$S_{yi} = \sum_{m=1}^{2N+1} w_{i,m}\{c_m^+ \exp(-k_0 q_m z) + c_m^- \exp[k_0 q_m (z-d)]\}, \qquad \text{eq. 19}$$

$$U_{xi} = \sum_{m=1}^{2N+1} v_{i,m}\{-c_m^+ \exp(-k_0 q_m z) + c_m^- \exp[k_0 q_m (z-d)]\}, \qquad \text{eq. 20}$$

where V=WQ.

Q is a diagonal matrix with elements $q_m$, which are the square roots of the 2N+1 eigenvalues of the matrix A, and W is the (2N+1)×(2N+1) matrix formed by the corresponding eigenvectors, with elements $w_{i,m}$.

The coefficients $c_m^+$, and $c_m^-$ are determined, along with the reflected and diffracted field amplitudes, by matching the tangential electric and magnetic fields at the boundaries between the two regions, z=0 and z=d (see FIG. 1).

At the z=0 boundary, eqs. 4 and 9 imply that $$E_{I,y}|_{z=0} = \exp[-jk_{x0}x] + \sum_{i=-N}^{N} R_i \exp(-jk_{xi}x) \qquad \text{eq. 21}$$

$$= \sum_{i=-N}^{N} S_{yi}(0)\exp(-jk_{xi}x)$$

$$= \sum_{i=-N}^{N} \exp(-jk_{xi}x)\left\{\sum_{m=1}^{2N+1} w_{i,m}\left[\begin{array}{c}c_m^+ + \\ c_m^- \exp(-k_0 q_m d)\end{array}\right]\right\}.$$

For the equality to hold in eq. 21, each of the components must be equal, so that $$\delta_{i0} + R_i = \sum_{m=1}^{2N+1} w_{i,m}[c_m^+ + c_m^- \exp(-k_0 q_m d)]. \qquad \text{eq. 22}$$

A similar argument can be applied to the magnetic field, which leads to $$j\left[n_I \cos\theta \delta_{i0} - \left(\frac{k_{I,zi}}{k_0}\right)R_i\right] = \sum_{m=1}^{2N+1} v_{i,m}[c_m^+ - c_m^- \exp(-k_0 q_m d)], \qquad \text{eq. 23}$$

at the z=0 boundary, where the magnetic field in region I was obtained from $$H_{I,x}|_{z=0} = -\left(\frac{j}{\omega\mu}\right)\frac{\partial E_{I,y}}{\partial z}\bigg|_{z=0} = \qquad \text{eq. 24}$$

$$\left(\frac{j}{\omega\mu}\right)\left\{jk_0 n_I \cos\theta \exp[-jk_{x0}x] - \sum_{i=-N}^{N} jk_{I,zi} R_i \exp(-jk_{xi}x)\right\}.$$

Note that it is also necessary to use the relationship $$\frac{1}{\omega\mu_0}\sqrt{\frac{\mu_0}{\varepsilon_0}} = \frac{c}{\omega} = \frac{1}{k_0},$$

where c is the speed of light in vacuum, when deriving eq. 23.

Eqs. 22 and 23 can be put in matrix form:

$$\left[\begin{array}{c}\delta_{i0}\\ jn_I \cos\theta \delta_{i0}\end{array}\right] + \left[\begin{array}{c}I\\ -jY_I\end{array}\right][R] = \left[\begin{array}{cc}W & WX\\ V & -VX\end{array}\right]\left[\begin{array}{c}c^+\\ c^-\end{array}\right], \qquad \text{eq. 25}$$

where $Y_I$ and X are diagonal matrices with elements ($k_{I,zi}/k_0$) and $\exp(-k_0 q_m d)$, respectively.

At the z=d boundary, $$\sum_{m=1}^{2N+1} w_{i,m}[c_m^+ \exp(-k_0 q_m d) + c_m^-] = T_i, \qquad \text{eq. 26}$$

$$\sum_{m=1}^{2N+1} v_{i,m}[c_m^+ \exp(-k_0 q_m d) - c_m^-] = j(k_{II,zi}/k_0)T_i, \qquad \text{eq. 27}$$

or $$\left[\begin{array}{cc}WX & W\\ VX & -V\end{array}\right]\left[\begin{array}{c}c^+\\ c^-\end{array}\right] = \left[\begin{array}{c}I\\ jY_{II}\end{array}\right][T], \qquad \text{eq. 28}$$

where $Y_{II}$ is a diagonal matrix with elements ($k_{II,zi}/k_0$).

Equations 25 and 28 are solved simultaneously for the coefficients $c_m^+$, and $c_m^-$, and diffracted amplitudes $R_i$ and $T_i$. It should be pointed out that there are many ways to solve the boundary equations. Here we will outline an efficient implementation of the enhanced transmission matrix—partial solution approach from M. G. Moharam, D. A. Pommet, E. B. Grann, and T. K. Gaylord, "Stable implementation of the rigorous coupled-wave analysis for surface-relief gratings: enhanced transmittance matrix approach," J. Opt. Soc. Am. A 12, 1077-1086 (1995), which can be used if only the reflected amplitudes are desired. Rewriting eq. 28, $$\left[\begin{array}{c}WX\\ VX\end{array}\right]c^+ = \left[\begin{array}{cc}-W & I\\ V & jY_{II}\end{array}\right]\left[\begin{array}{c}c^-\\ T\end{array}\right], \qquad \text{eq. 29}$$

or

-continued $$\begin{bmatrix} -W & I \\ V & jY_{II} \end{bmatrix}^{-1} \begin{bmatrix} WX \\ VX \end{bmatrix} c^+ = \begin{bmatrix} c^- \\ T \end{bmatrix}. \quad \text{eq. 30}$$

The top half of the matrix on the left side of eq. 30 is redefined as a new matrix, a:

$$\begin{bmatrix} a \\ b \end{bmatrix} \equiv \begin{bmatrix} -W & I \\ V & jY_{II} \end{bmatrix}^{-1} \begin{bmatrix} WX \\ VX \end{bmatrix} \quad \text{eq. 31}$$

so that $$ac^+ = c^-. \quad \text{eq. 32}$$

This allows us to rewrite eq. 25 as $$\begin{bmatrix} \delta_{i0} \\ jn_I\cos\theta\delta_{i0} \end{bmatrix} + \begin{bmatrix} I \\ -jY_I \end{bmatrix}[R] = \begin{bmatrix} W(I+Xa) \\ V(I-Xa) \end{bmatrix} c^+ = \begin{bmatrix} f \\ g \end{bmatrix} c^+, \quad \text{eq. 33}$$

where f≡W(I+Xa) and g≡V(I−Xa).

We first solve eq. 33 for the $c^+$ by multiplying the top half of the equations by $jY_I$ and adding that to the bottom half to eliminate R:

$$[jY_I f + g]c^+ = j(Y_I)_{0,0}\delta_{i0} + jn_I\cos\theta\delta_{i0}, \quad \text{eq. 34}$$

which is a (2N+1)×(2N+1) system of equations that are solved for the $c_m^+$. Note that $(Y_I)_{0,0}$ refers to the center element of the matrix $Y_I$, $(k_{I,z0}/k_0)$. The reflected amplitudes are the given by $$R = fc^+ - \delta_{i0}. \quad \text{eq. 35}$$

The diffracted efficiencies are obtained from $$DE_{ri} = R_i R_i^* \text{Re}\left(\frac{k_{I,zi}}{k_0 n_I \cos\theta}\right). \quad \text{eq. 36}$$

Note that for the zero order at normal incidence, $$R_{TE} = DE_{r0} = R_0 R_0^*. \quad \text{eq. 37}$$

The partial solution approach can be generalized to L layers if we start with $f_{L+1}=I$ and $g_{L+1}=jY_{II}$, where L+1 refers to the substrate, and use $$\begin{bmatrix} a_L \\ b_L \end{bmatrix} \equiv \begin{bmatrix} -W_L & f_{L+1} \\ V_L & g_{L+1} \end{bmatrix}^{-1} \begin{bmatrix} W_L X_L \\ V_L X_L \end{bmatrix}, \quad \text{eq. 38}$$

where $W_L$, $V_L$, come from the eigen-problem for layer L, but are otherwise defined as in the single layer case, and $X_L = \exp(-k_0 q_{m,L} d_L)$, with $d_L$ defined as the layer thickness.

Then we define $$\begin{bmatrix} f_L \\ g_L \end{bmatrix} \equiv \begin{bmatrix} W_L(I+X_L a_L) \\ V_L(I-X_L a_L) \end{bmatrix}, \quad \text{eq. 39}$$

substitute eq. 39 back into eq. 38 for the L-1 layer, and repeat the process until we obtain $f_1$ and $g_1$:

$$\begin{bmatrix} \delta_{i0} \\ jn_I\cos\theta\delta_{i0} \end{bmatrix} + \begin{bmatrix} I \\ -jY_I \end{bmatrix}[R] = \begin{bmatrix} W_1(I+X_1 a_1) \\ V_1(I-X_1 a_1) \end{bmatrix} c_1^+ = \begin{bmatrix} f_1 \\ g_1 \end{bmatrix} c_1^+, \quad \text{eq. 40}$$

which gives $$[jY_I f_1 + g_1]c_1^+ = j(Y_I)_{0,0}\delta_{i0} + jn_I\cos\theta\delta_{i0}. \quad \text{eq. 41}$$

Eq. 41 is solved for $c_1^+$, and the reflectance amplitudes are then $$R = f_1 c_1^+ - \delta_{i0}. \quad \text{eq. 42}$$

For the TM incident case, the magnetic field has only a y-component, while the electric field has x- and z-components. In the incident medium, $$H_{inc,y} = \exp[-jk_0 n_I(\sin\theta x + \cos\theta z)], \quad \text{eq. 43}$$

$$H_{I,y} = H_{inc,y} + \sum_{i=-\infty}^{\infty} R_i \exp[-j(k_{xi} - k_{I,zi}z)]. \quad \text{eq. 44}$$

In the substrate medium, $$H_{II,y} = \sum_{i=-\infty}^{\infty} T_i \exp\{-j[k_{xi}x + k_{II,zi}(z-d)]\}. \quad \text{eq. 45}$$

The tangential fields in the grating region are $$H_{gy} = \sum_{i=-\infty}^{\infty} U_{yi}(z)\exp(-jk_{xi}x) \quad \text{eq. 46}$$

$$E_{gx} = j\left(\frac{\mu_0}{\varepsilon_0}\right)^{1/2} \sum_{i=-\infty}^{\infty} S_{xi}(z)\exp(-jk_{xi}x). \quad \text{eq. 47}$$

The fields satisfy Maxwell's equation:

$$\vec{E} = \left(\frac{-j}{\omega\varepsilon_f n^2}\right)\nabla \times \vec{H}, \quad \text{eq. 48}$$

which leads to $$\frac{\partial H_{gy}}{\partial z} = -j\omega\varepsilon_f \varepsilon(x) E_{gx}, \quad \text{eq. 49}$$

$$\frac{\partial E_{gx}}{\partial z} = -j\omega\mu_f H_{gy} + \frac{\partial E_{gx}}{\partial x} \quad \text{eq. 50}$$

in the grating region. Eqs. 49 and 50 can be written in matrix form:

$$\begin{bmatrix} \partial U_y/\partial(z') \\ \partial S_x/\partial(z') \end{bmatrix} = \begin{bmatrix} 0 & E \\ B & 0 \end{bmatrix}\begin{bmatrix} U_y \\ S_x \end{bmatrix}, \quad \text{eq. 51}$$

where $z' = k_0 z$, and $$B = K_x E^{-1} K_x - 1. \quad \text{eq. 52}$$

$K_x$ and E are defined as before. Here we add a modification proposed independently by Lalanne and Morris (P. Lalanne and G. M. Morris, "Highly improved convergence of the coupled-wave method for TM polarization," J. Opt. Soc. Am. A 13, 779-784 (1996)), and Granet and Guizal (G. Granet and B. Guizal, "Efficient implementation of the coupled-wave method for metallic lamellar gratings in TM polarization," J. Opt. Soc. Am. A 13, 1019-1023 (1996)):

$$\begin{bmatrix} \partial U_y/\partial(z') \\ \partial S_x/\partial(z') \end{bmatrix} = \begin{bmatrix} 0 & Einv^{-1} \\ B & 0 \end{bmatrix} \begin{bmatrix} U_y \\ S_x \end{bmatrix}, \qquad \text{eq. 53}$$

where $Einv^{-1}$ is the inverse of the inverse permittivity matrix, Einv, with $(Einv)_{i,j}=(1/\epsilon)_{i,j}=a_{(i-j)}$, where $a_m$ are the Fourier coefficients of the inverse of the permittivity function. The modification of eq. 53 improves the convergence rate for the TM case significantly, especially for metallic materials.

Eq. 53 can be reduced to $$[\partial^2 U_y/\partial(z')^2] = [Einv^{-1}B][U_y]. \qquad \text{eq. 54}$$

Eq. 54 is solved in terms of the eigenvalues and eigenvectors of the matrix $Einv^{-1}B$, which gives for truncation order N $$U_{yi}(z) = \sum_{m=1}^{2N+1} w_{i,m}\{c_m^+ \exp(-k_0 q_m z) + c_m^- \exp[k_0 q_m(z-d)]\}, \qquad \text{eq. 55}$$

$$S_{xi}(z) = \sum_{m=1}^{2N+1} v_{i,m}\{-c_m^+ \exp(-k_0 q_m z) + c_m^- \exp(k_0 q_m(z-d))]\}, \qquad \text{eq. 56}$$

where V=EinvWQ.

Again, Q is a diagonal matrix with elements $q_m$, which are the square roots of the 2N+1 eigenvalues of the matrix $Einv^{-1}B$, and W is the (2N+1)×(2N+1) matrix formed by the corresponding eigenvectors, with elements $w_{i,m}$.

The tangential fields are matched at the two boundaries in a similar manner as before, leading to $$\delta_{i0} + R_i = \sum_{m=1}^{2N+1} w_{i,m}[c_m^+ + c_m^- \exp(-k_0 q_m d)], \qquad \text{eq. 57}$$

$$j\left[\left(\frac{\cos\theta}{n_I}\right)\delta_{i0} - \left(\frac{k_{I,zi}}{k_0 n_I^2}\right)R_i\right] = \sum_{m=1}^{2N+1} v_{i,m}[c_m^+ - c_m^- \exp(-k_0 q_m d)], \qquad \text{eq. 58}$$

or in matrix form:

$$\begin{bmatrix} \delta_{i0} \\ j\delta_{i0}\cos\theta/n_I \end{bmatrix} + \begin{bmatrix} I \\ -jZ_I \end{bmatrix}[R] = \begin{bmatrix} W & WX \\ V & -VX \end{bmatrix}\begin{bmatrix} c^+ \\ c^- \end{bmatrix}, \qquad \text{eq. 59}$$

where $Z_I$ and X are diagonal matrices with elements $(k_{I,zi}/k_0 n_I^2)$ and $\exp(-k_0 q_m d)$, respectively.

At the z=d boundary, $$\sum_{m=1}^{2N+1} w_{i,m}[c_m^+ \exp(-k_0 q_m d) + c_m^-] = T_i, \qquad \text{eq. 60}$$

$$\sum_{m=1}^{2N+1} v_{i,m}[c_m^+ \exp(-k_0 q_m d) + c_m^-] = j\left(\frac{k_{II,zi}}{k_0 n_{II}^2}\right)T_i, \qquad \text{eq. 61}$$

or in matrix form:

$$\begin{bmatrix} WX & W \\ VX & -V \end{bmatrix}\begin{bmatrix} c^+ \\ c^- \end{bmatrix} = \begin{bmatrix} I \\ jZ_{II} \end{bmatrix}[T], \qquad \text{eq. 62}$$

where $Z_{II}$ is a diagonal matrix with elements $(k_{II,zi}/k_0 n_{II}^2)$.

The boundary problem is solved in the same manner as before, giving $$[jZ_I f + g]c^+ = j(Z_I)_{0,0}\delta_{i0} + j\frac{\cos\theta}{n_I}\delta_{i0}, \qquad \text{eq. 63}$$

for the coefficients $c^+$, and finally $$R = fc^+ - \delta_{i0}. \qquad \text{eq. 64}$$

for the reflected amplitudes.

For L layers, the recursion is the same as in the TE case, giving $$[jZ_I f_1 + g_1]c_1^+ = j(Z_I)_{0,0}\delta_{i0} + j\frac{\cos\theta}{n_I}\delta_{i0}. \qquad \text{eq. 65}$$

for $c_1^+$, and $$R = f_1 c_1^+ - \delta_{i0}. \qquad \text{eq. 66}$$

for the diffracted amplitudes.

The preceding description can be applied to polarized reflectance data collected in the phi=0 mount, or to un-polarized reflectance by use of eq. 1. Typically, the reflectance data is used to optimize the parameters of a theoretical model representative of the presumed structure, using one of many common algorithms, such as the Levenberg-Marquardt or Simplex algorithms (see W. H. Press, S. A. Teukolsky, W. T. Vetterling, and B. P. Flannery, *Numerical Recipes in C* (2$^{nd}$ *Edition*), Cambridge University Press, Cambridge, 1992, for example). The model calculation is performed at each regression step using the above RCW formulation. Alternately, a library database of spectra corresponding to the entire parameter space expected for the model is pre-generated. In this case the regression retrieves the required spectrum from the library at each step, or any of a variety of search mechanisms are used during the measurement to find the best match to the actual reflectance.

The RCW calculation is dominated by a (2N+1)×(2N+1) eigen-problem and a (2N+1)×(2N+1) boundary problem, as well as several (2N+1)×(2N+1) matrix multiplications. All of these operations are order $n^3$, where n is the matrix size, which means that doubling the truncation order results in an approximately 8-fold increase in overall computation time. For large truncation order the calculation time can become significant.

The truncation order is dependent on the structure being simulated. Generally, larger pitch to wavelength ratios and larger contrast between line and space optical properties will require larger truncation order to converge. In addition, complicated feature profiles can require a large number of layer slices to correctly approximate the line shape. All said, for some structures the required RCW calculations can become prohibitively time consuming.

A reduction of the required computation steps for a given truncation order, N, will directly address the issue, since it will reduce the calculation time everywhere. In particular, the order $n^3$ behavior of the RCW method means that reducing the matrix sizes for given truncation order can have a dramatic effect on the computation speed. It is possible to do this by exploiting the symmetry for certain incidence and grating conditions.

A method for reducing the matrix size from 2N+1 to N+1 in the case of normal incidence will now be described.

For normal incidence, we have $$k_{xi} = -ik_0(\lambda_0/\Lambda) = -2\pi i/\Lambda, \quad \text{eq. 67}$$

$$k_{xi} = -k_{x,-i} \quad \text{eq. 68}$$

$$k_{I,zi} = k_{I,z,-i} \quad \text{eq. 69}$$

from eqs. 7 and 8. If the grating is symmetric, there are additional conditions imposed on the fields:

$$E_{y,i} = E_{y,-i} \quad \text{eq. 70}$$

$$H_{x,i} = H_{x,-i} \quad \text{eq. 71}$$

for TE polarization, and $$E_{x,i} = E_{x,-i} \quad \text{eq. 72}$$

$$H_{y,i} = H_{y,-i}. \quad \text{eq. 73}$$

for TM polarization, where the subscript i refers to the expansion term, which in the incident region, corresponds to the diffraction order.

These conditions can be reasoned out from symmetry arguments, or by experimentation with calculations performed using the more general RCW method presented above. The symmetry relationships are valid in all regions of the grating problem. There is also a 180 degree phase difference between opposite odd orders, but this can be ignored when not considering interference between multiple gratings.

Applying the above relations to the various regions in the 2-D grating problem for the TE case:

$$R_i = R_{-i} \quad \text{eq. 74}$$

$$T_i = T_{-i} \quad \text{eq. 75}$$

in regions I and II, and $$S_{yi} = S_{y,-i} \quad \text{eq. 76}$$

$$U_{xi} = U_{x,-i} \quad \text{eq. 77}$$

for the fields in the grating region. These conditions can be applied directly to the Fourier expansions of eqs. 2-6.

We first note that eq. 2, the incident wave has no x-dependence, and is simply $$E_{inc,y} = \exp(-jk_0 n_I z). \quad \text{eq. 78}$$

Applying eqs. 74 and 78 to eq. 3 gives $$E_{I,y} = E_{inc,y} + \sum_{i=-\infty}^{\infty} R_i \exp[-j(k_{xi}x - k_{I,zi}z)] \quad \text{eq. 79}$$

$$= E_{inc,y} + R_0 \exp(jk_{I,z0}z) + \sum_{i=1}^{\infty} R_i \exp[-j(k_{xi}x - k_{I,zi}z)] + \sum_{i=-\infty}^{-1} R_i \exp[-j(k_{xi}x - k_{I,zi}z)]$$

$$= E_{inc,y} + R_0 \exp(jk_{I,z0}z) + \sum_{i=1}^{\infty} R_i \exp[-j(k_{xi}x - k_{I,zi}z)] + \sum_{i=1}^{\infty} R_{-i} \exp[-j(k_{x,-i}x - k_{I,z,-i}z)]$$

$$= E_{inc,y} + R_0 \exp(jk_{I,z0}z) + \sum_{i=1}^{\infty} R_i \exp[-jk_{xi}x + jk_{I,zi}z] + \sum_{i=0}^{\infty} R_i \exp[jk_{xi}x + jk_{I,zi}z]$$

$$= E_{inc,y} + R_0 \exp(jk_{I,z0}z) + \sum_{i=1}^{\infty} R_i \exp(jk_{I,zi}z)[\exp(-jk_{xi}x) + \exp(jk_{xi}x)]$$

$$= E_{inc,y} + R_0 \exp(jk_{I,z0}z) + \sum_{i=1}^{\infty} 2R_i \exp(jk_{I,zi}z) \cos(jk_{xi}x).$$

At z=0, eq. 79 becomes simply a Fourier cosine series expansion of the field at the boundary:

$$E_{I,y}(z=0) = \quad \text{eq. 80}$$

$$1 + R_0 + \sum_{i=1}^{\infty} 2R_i \cos(jk_{xi}x) = 1 + R_0 + \sum_{i=1}^{\infty} 2R_i \cos(j2\pi i x/\Lambda).$$

Similarly, at the z=d boundary:

$$E_{II,y}(z=d) = T_0 + \sum_{i=1}^{\infty} 2T_i \cos(jk_{xi}x), \quad \text{eq. 81}$$

And inside the grating region, $$E_{gy} = S_{y0}(z) + \sum_{i=1}^{\infty} 2S_{yi}(z) \cos(jk_{xi}x), \quad \text{eq. 82}$$

$$H_{gx} = -j\left(\frac{\varepsilon_f}{\mu_f}\right)^{1/2} \left\{ U_{x0}(z) + \sum_{i=1}^{\infty} 2U_{xi}(z) \cos(jk_{xi}x) \right\}. \quad \text{eq. 83}$$

The fact that the fields can be reduced to cosine series is a direct consequence of the even symmetry of the diffraction problem with respect to the x coordinate under the normal incidence condition. For a given truncation order, N, the reduced expansions contain exactly the same information, but with N+1 unknowns instead of 2N+1.

To show that the form of the boundary problem need not be modified, we first assume that the size of the eigen-problem can be reduced to (N+1)×(N+1), and otherwise has the same form as eqs. 19 and 20, as shown below. Matching the y-components of the electric field at the z=0 boundary:

$$1 + R_0 + \sum_{i=1}^{\infty} 2R_i \cos(jk_{xi}x) = S_{y0}(0) + \sum_{i=1}^{\infty} 2S_{yi}(0)\cos(jk_{xi}x) \quad \text{eq. 84}$$

$$= \sum_{m=1}^{N+1} w_{0,m}[c_m^+ +$$

$$c_m^- \exp(-k_0 q_m d)] +$$

$$\sum_{i=1}^{N} 2\cos(jk_{xi}x) \sum_{m=1}^{N+1} w_{i,m}[c_m^+ +$$

-continued
$$c_m^- \exp(-k_0 q_m d)].$$

Since this condition holds for all x, terms with the same $\cos(jk_{xi}x)$ on each side must be equal:

$$1 + R_0 = \sum_{m=1}^{N+1} w_{0,m}[c_m^+ + c_m^- \exp(-k_0 q_m d)] \qquad \text{eq. 85}$$

$$2R_i = \sum_{i=1}^{N+1} 2w_{i,m}[c_m^+ + c_m^- \exp(-k_0 q_m d)], \qquad \text{eq. 86}$$

or $$\delta_{i0} + R_i = \sum_{m=1}^{N+1} w_{i,m}[c_m^+ + c_m^- \exp(-k_0 q_m d)] \qquad \text{eq. 87}$$

Which is the same as eq. 22, except that the index i runs from 0 to N, and the index m runs from 1 to N+1.

The magnetic field at the z=0 boundary in region I is $$H_{I,x}|_{z=0} = -\left(\frac{j}{\omega\mu}\right)\frac{\partial E_{I,y}}{\partial z}\bigg|_{z=0} = \qquad \text{eq. 88}$$

$$\left(\frac{j}{\omega\mu}\right)\left[jk_0 n_I - jk_0 n_I R_0 - \sum_{i=1}^{\infty} jk_{I,zi} 2R_i \cos(jk_{xi}x)\right],$$

which leads to $$j\left[n_I \delta_{i0} - \left(\frac{k_{I,zi}}{k_0}\right)R_i\right] = \sum_{m=1}^{N+1} v_{i,m}[c_m^+ - c_m^- \exp(-k_0 q_m d)] \qquad \text{eq. 89}$$

for the magnetic field condition.
Similarly, for the z=d boundary, $$\sum_{m=1}^{N+1} w_{i,m}[c_m^+ \exp(-k_0 q_m d) + c_m^-] = T_i, \qquad \text{eq. 90}$$

$$\sum_{m=1}^{N+1} v_{i,m}[c_m^+ \exp(-k_0 q_m d) + c_m^-] = j\left(\frac{k_{II,zi}}{k_0 n_{II}^2}\right)T_i. \qquad \text{eq. 91}$$

Eqs. 87, 89, 90, and 91 obviously lead to the same boundary problem as eqs. 25 and 28, but now with (N+1)×(N+1) sets of equations instead of (2N+1)×(2N+1). The steps outlined in eqs. 29-42 can still be used to solve the boundary problem. Alternately, since the form of the boundary problem is unchanged from the conventional formulation, any number of other well-known techniques, such as the R-matrix, T-matrix, S-matrix, or the more recent enhanced R-matrix (E. L. Tan, "Enhanced R-matrix algorithms for multilayered diffraction gratings," Appl. Opt. 45, 4803-4809 (2006) and hybrid-matrix algorithms (E. L. Tan, "Hybrid-matrix algorithm for rigorous coupled-wave analysis of multilayered diffraction gratings," J. Mod. Opt. 53, 417-428 (2006)), can be easily applied to the reduced multiple layer diffraction problem. The form of the boundary problem differs from the reduction discussed in U.S. Pat. No. 6,898,537, in that the U.S. Pat. No. 6,898,537 teaches that every nonzero diffracted reflectance coefficient must be multiplied by a factor of two.

To show how to reduce the eigen-problem to the form we assumed above, we start by applying eq. 76 to eq. 18. The rows of eq. 18 can be written in the form $$\frac{\partial^2 S_{yi}}{\partial (z')^2} = \left(\frac{k_{xi}^2}{k_0^2}\right)S_{yi} - \sum_{m=-\infty}^{\infty} E_{i,m} S_{ym}. \qquad \text{eq. 92}$$

For the i=0 term, $$\frac{\partial^2 S_{y0}}{\partial (z')^2} = -\sum_{m=-\infty}^{\infty} E_{0,m} S_{ym} \qquad \text{eq. 93}$$

$$= -E_{0,0} S_{y0} - \sum_{m=-\infty}^{-1} E_{0,m} S_{ym} - \sum_{m=1}^{\infty} E_{0,m} S_{ym}$$

$$= -E_{0,0} S_{y0} - \sum_{m=1}^{\infty} E_{0,-m} S_{ym} - \sum_{m=1}^{\infty} E_{0,m} S_{ym}$$

$$= -E_{0,0} S_{y0} - \sum_{m=1}^{\infty} (E_{0,-m} + E_{0,m}) S_{ym}$$

$$= -E_{0,0} S_{y0} - \sum_{m=1}^{\infty} 2E_{0,m} S_{ym}$$

so $$\frac{\partial^2 S_{y0}}{\partial (z')^2} = -E_{0,0} S_{y0} - \sum_{m=1}^{\infty} 2E_{0,m} S_{ym}, \; i = 0,$$

where we have used the fact that $k_{x0}=0$, and $$E_{i,j} = E_{-i,-j}, \qquad \text{eq. 94}$$

which follows from eq. 17 for a symmetric grating.

For i≠0, we use eq. 76 to derive $$\frac{\partial^2 S_{yi}}{\partial (z')^2} = \frac{\partial^2 S_{y-i}}{\partial (z')^2}, \qquad \text{eq. 95}$$

and add the i th and −i th rows:

$$2\frac{\partial^2 S_{yi}}{\partial (z')^2} = \left(\frac{k_{xi}^2}{k_0^2}\right)S_{yi} + \left(\frac{k_{x-i}^2}{k_0^2}\right)S_{y-i} - \sum_{m=-\infty}^{\infty} E_{i,m} S_{ym} - \qquad \text{eq. 96}$$

$$\sum_{m=-\infty}^{\infty} E_{-i,m} S_{ym}$$

$$= \left(\frac{k_{xi}^2}{k_0^2}\right)S_{yi} + \left(\frac{k_{xi}^2}{k_0^2}\right)S_{yi} - \sum_{m=-\infty}^{\infty} E_{i,m} S_{ym} -$$

$$\sum_{m=-\infty}^{\infty} E_{-i,m} S_{ym}$$

$$= 2\left(\frac{k_{xi}^2}{k_0^2}\right)S_{yi} - E_{i,0} S_{y0} - \sum_{m=1}^{\infty} E_{i,m} S_{ym} -$$

$$\sum_{m=-\infty}^{-1} E_{i,m} S_{ym} - E_{-i,0} S_{y,0} - \sum_{m=1}^{\infty} E_{-i,m} S_{ym} -$$

$$\sum_{m=-\infty}^{-1} E_{-i,m} S_{ym}$$

-continued $$= 2\left(\frac{k_{xi}^2}{k_0^2}\right)S_{yi} - 2E_{i,0}S_{y,0} - \sum_{m=1}^{\infty} E_{i,m}S_{ym} -$$

$$\sum_{m=1}^{\infty} E_{i,-m}S_{ym} - \sum_{m=1}^{\infty} E_{-i,m}S_{ym} - \sum_{m=1}^{\infty} E_{-i,-m}S_{ym}$$

$$= 2\left(\frac{k_{xi}^2}{k_0^2}\right)S_{yi} - 2E_{i,0}S_{y,0} - 2\sum_{m=1}^{\infty} E_{i,m}S_{ym} -$$

$$2\sum_{m=1}^{\infty} E_{i,-m}S_{ym}$$

$$= 2\left(\frac{k_{xi}^2}{k_0^2}\right)S_{yi} - 2E_{i,0}S_{y,0} - 2\sum_{m=1}^{\infty} (E_{i,m} + E_{i,-m})S_{ym},$$

giving $$\frac{\partial^2 S_{yi}}{\partial (z')^2} = \left(\frac{k_{xi}^2}{k_0^2}\right)S_{yi} - E_{i,0}S_{y,0} - \sum_{m=1}^{\infty} (E_{i,m} + E_{i,-m})S_{ym}, \ i > 0.$$

Eqs. 93 and 96 lead to matrix equations with the same form as eq. 18, but with (N+1)×(N+1) sized matrices instead of the original (2N+1)×(2N+1) sized matrices. The permittivity matrix E is replaced with $$E_{reduced} = \begin{bmatrix} E_{0,0} & 2E_{0,1} & 2E_{0,2} & \cdots \\ E_{1,0} & (E_{1,1} + E_{1,-1}) & (E_{1,2} + E_{1,-2}) & \cdots \\ E_{2,0} & (E_{2,1} + E_{2,-1}) & (E_{2,2} + E_{2,-2}) & \cdots \\ \vdots & & & \ddots \end{bmatrix}. \quad \text{eq. 97}$$

That is, the first column of the reduced matrix is replaced by $E_{i,0}$ from the original matrix, and the other elements i,j are $E_{i,j}+E_{i,-j}$, in terms of the elements of the old matrix, with i,j≥0. Eq. 97 can be compared with eq. 26 from the U.S. Pat. No. 6,898,537, which does not include the $E_{i,-j}$ term for reduced matrix elements when i+j is greater than the truncation order, N. This omission is not suggested in that reference, since the corresponding unreduced matrix includes the $\epsilon_{2N}$ permittivity coefficients for a given N.

The matrix $K_x$ is simply replaced by an (N+1)×(N+1) diagonal matrix consisting of the 0 and positive terms of the original $K_x$.

Therefore, we have for the new eigen-problem, $$\left[\frac{\partial^2 S_y}{\partial (z')^2}\right] = [A_{reduced}][S_y], \quad \text{eq. 98}$$

with $$A_{reduced} = K_x^2 - E_{reduced} \quad \text{eq. 99}$$

Eq. 99 is solved in a manner similar to eq. 18:

$$S_{yi} = \sum_{m=1}^{N+1} w_{i,m}\{c_m^+\exp(-k_0 q_m z) + c_m^-\exp[k_0 q_m(z-d)]\} \quad \text{eq. 100}$$

$$U_{xi} = \sum_{m=1}^{N+1} v_{i,m}\{-c_m^+\exp(-k_0 q_m z) + c_m^-\exp[k_0 q_m(z-d)]\} \quad \text{eq. 101}$$

where V=WQ, Q is a diagonal matrix with elements $q_m$, which are the square roots of the N+1 eigenvalues of the matrix $A_{reduced}$, and W is the (N+1)×(N+1) matrix formed by the corresponding eigenvectors, with elements $w_{i,m}$.

The size of the eigen-problem and boundary problem are therefore reduced to (N+1)×(N+1) for a given truncation order, N. Now we determine N+1 reflected amplitudes, $R_i$, i=0, ..., N, but in light of the fact that $R_{-i}=R_i$, we have determined the same information as in the conventional formulation. It is important to note that no approximations were made, except for the usual series truncations. For given truncation order, N, the calculation gives an identical result, but is faster by a factor of approximately 8 compared to the standard RCW formulation.

For the TM case, just as for the TE case, the boundary problem reduces to the same form as the conventional formulation, but with an (N+1)×(N+1) system of equations instead of a (2N+1)×(2N+1) system. Again, we determine $R_i$, i=0, ..., N with a factor of 8 reduction in overall computation time. The task remaining is to determine the reduced eigen-problem for the TM case.

We again have eqs. 67-69, eqs. 74, 75, and 94, but this time use $$S_{xi} = S_{x,-i} \quad \text{eq. 102}$$

$$U_{yi} = U_{y,-i} \quad \text{eq. 103}$$

in the grating region. We can reduce the matrix $Einv^{-1}B$ by applying these relations to eq. 54 directly, but this will lead to an unnecessary (2N+1)×(2N+1) matrix multiplication to find the elements of $Einv^{-1}B$. We instead go back to eq. 53 and reduce the matrices separately, resulting in an (N+1)×(N+1) multiplication instead.

We start with the first row of eq. 53, the rows of which are:

$$\frac{\partial U_{yi}}{\partial (z')} = \sum_{m=-\infty}^{\infty} (Einv^{-1})_{i,m} S_{xm} \quad \text{eq. 104}$$

For i=0, $$\frac{\partial U_{y0}}{\partial (z')} = (Einv^{-1})_{0,0} S_{x0} + \sum_{m=1}^{\infty} (Einv^{-1})_{0,m} S_{xm} + \quad \text{eq. 105}$$

$$\sum_{m=-\infty}^{-1} (Einv^{-1})_{0,m} S_{xm}$$

$$= (Einv^{-1})_{0,0} S_{x0} + \sum_{m=1}^{\infty} (Einv^{-1})_{0,m} S_{xm} +$$

$$\sum_{m=1}^{\infty} (Einv^{-1})_{0,-m} S_{xm}$$

$$= (Einv^{-1})_{0,0} S_{x0} + \sum_{m=1}^{\infty} [(Einv^{-1})_{0,m} +$$

$$(Einv^{-1})_{0,-m}] S_{xm},$$

or $$\frac{\partial U_{y0}}{\partial (z')} = (Einv^{-1})_{0,0} S_{x0} + \sum_{m=1}^{\infty} 2(Einv^{-1})_{0,m} S_{xm}, \ i = 0,$$

where we use $$(Einv^{-1})_{i,j} = (Einv^{-1})_{-i,-j} \quad \text{eq. 106}$$

for a symmetric grating. For $i \neq 0$, we again add the i th and $-i$ th rows:

$$2\frac{\partial U_{yi}}{\partial(z')} = \sum_{m=-\infty}^{\infty}(Einv^{-1})_{i,m}S_{xm} + \sum_{m=-\infty}^{\infty}(Einv^{-1})_{-i,m}S_{xm} \quad \text{eq. 107}$$

$$= (Einv^{-1})_{i,0}S_{x0} + \sum_{m=1}^{\infty}(Einv^{-1})_{i,m}S_{xm} +$$

$$\sum_{m=-\infty}^{-1}(Einv^{-1})_{i,m}S_{xm} + (Einv^{-1})_{-i,0}S_{x0} +$$

$$\sum_{m=1}^{\infty}(Einv^{-1})_{-i,m}S_{xm} + \sum_{m=-\infty}^{-1}(Einv^{-1})_{-i,m}S_{xm}$$

$$= (Einv^{-1})_{i,0}S_{x0} + (Einv^{-1})_{-i,0}S_{x0} +$$

$$\sum_{m=1}^{\infty}(Einv^{-1})_{i,m}S_{xm} + \sum_{m=1}^{\infty}(Einv^{-1})_{i,-m}S_{xm} +$$

$$\sum_{m=1}^{\infty}(Einv^{-1})_{-i,m}S_{xm} + \sum_{m=1}^{\infty}(Einv^{-1})_{-i,-m}S_{xm}$$

$$= 2(Einv^{-1})_{i,0}S_{x0} + \sum_{m=1}^{\infty}2(Einv^{-1})_{i,m}S_{xm} +$$

$$\sum_{m=1}^{\infty}2(Einv^{-1})_{i,-m}S_{xm}$$

$$= 2(Einv^{-1})_{i,0}S_{x0} + \sum_{m=1}^{\infty}2[(Einv^{-1})_{i,m} + (Einv^{-1})_{i,-m}]S_{xm}$$

so that $$\frac{\partial U_{yi}}{\partial(z')} = (Einv^{-1})_{i,0}S_{x0} + \sum_{m=1}^{\infty}\left[\begin{array}{c}(Einv^{-1})_{i,m} + \\ (Einv^{-1})_{i,-m}\end{array}\right]S_{xm}, \, i > 0.$$

In matrix form, $$Einv^{-1}_{reduced} = \begin{bmatrix} (Einv^{-1})_{0,0} & 2(Einv^{-1})_{0,1} & 2(Einv^{-1})_{0,2} & \cdots \\ (Einv^{-1})_{1,0} & [(Einv^{-1})_{1,1}+(Einv^{-1})_{1,-1}] & [(Einv^{-1})_{1,2}+(Einv^{-1})_{1,-2}] & \cdots \\ (Einv^{-1})_{2,0} & [(Einv^{-1})_{2,1}+(Einv^{-1})_{2,-1}] & [(Einv^{-1})_{2,2}+(Einv^{-1})_{2,-2}] & \cdots \\ \vdots & & & \ddots \end{bmatrix},$$

where the first column of the reduced matrix is replaced by $(Einv^{-1})_{0,0}$ from the original matrix, and the rest of the elements i,j are $(Einv^{-1})_{i,j} + (Einv^{-1})_{i,-j}$, in terms of the elements of the old matrix, with $i,j \geq 0$.

For the matrix B, we reduce $$\frac{\partial S_{xi}}{\partial(z')} = \frac{k_{xi}}{k_0}\sum_{m=-\infty}^{\infty}(E^{-1})_{i,m}\frac{k_{xm}}{k_0}U_{ym} - U_{yi}. \quad \text{eq. 109}$$

For i=0, $$\frac{\partial S_{x0}}{\partial(z')} = -U_{y0}, \quad \text{eq. 110}$$

since $k_{x0}=0$. For $i \neq 0$, adding the i th and $-i$ th rows:

$$2\frac{\partial S_{xi}}{\partial(z')} = \frac{k_{xi}}{k_0}\sum_{m=-\infty}^{\infty}(E^{-1})_{i,m}\frac{k_{xm}}{k_0}U_{ym} + \quad \text{eq. 111}$$

$$\frac{k_{x-i}}{k_0}\sum_{m=-\infty}^{\infty}(E^{-1})_{-i,m}\frac{k_{xm}}{k_0}U_{ym} - 2U_{yi}$$

$$= \frac{k_{xi}}{k_0}\sum_{m=-\infty}^{\infty}(E^{-1})_{i,m}\frac{k_{xm}}{k_0}U_{ym} -$$

$$\frac{k_{xi}}{k_0}\sum_{m=-\infty}^{\infty}(E^{-1})_{-i,m}\frac{k_{xm}}{k_0}U_{ym} - 2U_{yi}$$

$$= \frac{k_{xi}}{k_0}\left\{\sum_{m=1}^{\infty}(E^{-1})_{i,m}\frac{k_{xm}}{k_0}U_{ym} + \sum_{m=-\infty}^{-1}(E^{-1})_{i,m}\frac{k_{xm}}{k_0}U_{ym} - \sum_{m=1}^{\infty}(E^{-1})_{-i,m}\frac{k_{xm}}{k_0}U_{ym} - \sum_{m=-\infty}^{-1}(E^{-1})_{-i,m}\frac{k_{xm}}{k_0}U_{ym}\right\} - 2U_{yi}$$

$$= \frac{k_{xi}}{k_0}\left\{\sum_{m=1}^{\infty}(E^{-1})_{i,m}\frac{k_{xm}}{k_0}U_{ym} + \sum_{m=1}^{\infty}(E^{-1})_{i,-m}\frac{k_{x-m}}{k_0}U_{ym} - \sum_{m=1}^{\infty}(E^{-1})_{-i,m}\frac{k_{xm}}{k_0}U_{ym} - \sum_{m=1}^{\infty}(E^{-1})_{-i,-m}\frac{k_{x-m}}{k_0}U_{ym}\right\} - 2U_{yi}$$

$$= \frac{k_{xi}}{k_0}\left\{\sum_{m=1}^{\infty}(E^{-1})_{i,m}\frac{k_{xm}}{k_0}U_{ym} - \sum_{m=1}^{\infty}(E^{-1})_{i,-m}\frac{k_{xm}}{k_0}U_{ym} - \sum_{m=1}^{\infty}(E^{-1})_{-i,m}\frac{k_{xm}}{k_0}U_{ym} + \sum_{m=1}^{\infty}(E^{-1})_{-i,-m}\frac{k_{xm}}{k_0}U_{ym}\right\} - 2U_{yi}$$

$$= \frac{k_{xi}}{k_0}\sum_{m=1}^{\infty}\left[\begin{array}{c}(E^{-1})_{i,m}+(E^{-1})_{-i,-m} - \\ (E^{-1})_{i,-m}-(E^{-1})_{-i,m}\end{array}\right]\frac{k_{xm}}{k_0}U_{ym} - 2U_{yi}$$

$$= \frac{k_{xi}}{k_0}\sum_{m=1}^{\infty}[2(E^{-1})_{i,m}-2(E^{-1})_{i,-m}]\frac{k_{xm}}{k_0}U_{ym} - 2U_{yi},$$

-continued or $$\frac{\partial S_{xi}}{\partial(z')} = \frac{k_{xi}}{k_0}\sum_{m=1}^{\infty}[(E^{-1})_{i,m}-(E^{-1})_{i,-m}]\frac{k_{xm}}{k_0}U_{ym} - U_{yi},$$

$i > 0$.

From eqs. 110 and 111, the reduced matrix for $K_x E^{-1} K_x$ has zeros in the first row and column, and the elements $$\frac{k_{xi}}{k_0}[(E^{-1})_{i,j}-(E^{-1})_{i,-j}]\frac{k_{xj}}{k_0}$$

otherwise, with i,j>0. In matrix form, $$(K_x E^{-1} K_x)_{reduced} = \begin{bmatrix} 0 & 0 & 0 & \cdots \\ 0 & \frac{k_{x1}}{k_0}[(E^{-1})_{1,1} - (E^{-1})_{1,-1}]\frac{k_{x1}}{k_0} & \frac{k_{x1}}{k_0}[(E^{-1})_{1,2} - (E^{-1})_{1,-2}]\frac{k_{x2}}{k_0} & \cdots \\ 0 & \frac{k_{x2}}{k_0}[(E^{-1})_{2,1} - (E^{-1})_{2,-1}]\frac{k_{x1}}{k_0} & \frac{k_{x2}}{k_0}[(E^{-1})_{2,2} - (E^{-1})_{2,-2}]\frac{k_{x2}}{k_0} & \cdots \\ \vdots & & & \ddots \end{bmatrix}$$

eq. 112

This gives $$B_{reduced} = (K_x E^{-1} K_x)_{reduced} - I,$$  eq. 113 where I is an (N+1)×(N+1) identity matrix, $$\begin{bmatrix} \partial U_y / \partial(z') \\ \partial S_x / \partial(z') \end{bmatrix} = \begin{bmatrix} 0 & (Einv^{-1})_{reduced} \\ B_{reduced} & 0 \end{bmatrix} \begin{bmatrix} U_y \\ S_x \end{bmatrix},$$  eq. 114 which reduces to $$[\partial^2 U_y / \partial(z')^2] = [(Einv^{-1})_{reduced} B_{reduced}][U_y].$$  eq. 115

The solution to eq. 115 is $$U_{yi} = \sum_{m=1}^{N+1} w_{i,m} \{c_m^+ \exp(-k_0 q_m z) + c_m^- \exp[k_0 q_m (z-d)]\}$$  eq. 116

$$S_{xi} = \sum_{m=1}^{N+1} v_{i,m} \{-c_m^+ \exp(-k_0 q_m z) + c_m^- \exp[k_0 q_m (z-d)]\}.$$  eq. 117

Here we first define Q as a diagonal matrix with elements $q_m$, which are the square roots of the N+1 eigenvalues of the matrix $(Einv^{-1})_{reduced} B_{reduced}$, and W as the (N+1)×(N+1) matrix formed by the corresponding eigenvectors, with elements $w_{i,m}$.

To find the matrix V, we can substitute eqs. 116 and 117 into the top half of eq. 114 to obtain $$WQ = (Einv^{-1})_{reduced} V,$$  eq. 118 so $$V = [(Einv^{-1})_{reduced}]^{-1} WQ = Einv_{reduced} WQ.$$  eq. 119

Eq. 119 suggests a way to further improve the efficiency of the algorithm for the TM case. A (2N+1)×(2N+1) matrix inversion is required to find the elements of $Einv^{-1}$, which is then reduced and inverted (an (N+1)×(N+1) matrix inversion) to find $[(Einv^{-1})_{reduced}]^{-1}$. But since $[(Einv^{-1})_{reduced}]^{-1} = Einv_{reduced}$, we may as well find $Einv_{reduced}$ through application of eqs. 105 and 107 (with Einv in place of $Einv^{-1}$), and invert that matrix to find $(Einv^{-1})_{reduced}$. This still involves an (N+1)×(N+1) matrix inversion, but eliminates the (2N+1)×(2N+1) matrix inversion, and we still end up with $Einv_{reduced}$ as well as $(Einv^{-1})_{reduced}$ to use in eqs. 114 and 115.

In other words, instead of starting with the unreduced $Einv^{-1}$ matrix, start by forming Einv from the inverse permittivity components and apply $$\frac{\partial U_{y0}}{\partial(z')} = (Einv)_{0,0} S_{x0} + \sum_{m=1}^{\infty} 2(Einv)_{0,m} S_{xm}, \quad i = 0$$  eq. 120 and $$\frac{\partial U_{yi}}{\partial(z')} = (Einv)_{i,0} S_{x0} + \sum_{m=1}^{\infty} [(Einv)_{i,m} + (Einv)_{i,-m}] S_{xm},$$  eq. 121

$i > 0$ to find $Einv_{reduced}$ use in eq. 119, and the inverse of this (N+1)×(N+1) matrix becomes $(Einv^{-1})_{reduced}$ for eq. 115. With this enhancement and the use of eq. 112 for the reduced B matrix, there remains only one (2N+1)×(2N+1) matrix operation to invert the original permittivity matrix, E, for the TM case. All other matrix operations involve matrices of size N+1. Since matrix inversion scales as $N^3$, The elimination of one of the (2N+1)×(2N+1) inversions can have a large impact on computation time, especially for large truncation order N.

Eqs. 120 and 121 can be compared with eq. 42 from U.S. Pat. No. 6,898,537, which again neglects inverse permittivity components when i+j>N.

The above reductions for the TE and TM case can be applied to polarized incident light, but can also be used with un-polarized light, by making use of eq. 1. This is particularly advantageous for obtaining below DUV reflectance data for the reasons already mentioned above. A typical below DUV-Vis optical CD measurement would proceed as follows:

1) Pattern recognition and a separate vision system move the r-θ stage to the desired grating structure.
2) Un-polarized light is directed on the structure from a normal incidence configuration, and the specular reflection recorded.
3) A theoretical model of the assumed grating structure is constructed.
4) A regression analysis is performed—either using real-time model calculations or extracting the model curve from a library database—to optimize the structural parameters of the theoretical model, based on the measured reflectance. The above reduced calculation for TE and TM polarized light, along with eq. 1 may be used to perform the model calculations.

The optimized parameters at the end of the analysis are the measurement result. The above steps, especially when used with a pre-generated library, can ordinarily be carried out in only a few seconds per measurement. The particular configuration with normally incident un-polarized light removes difficult issues such as polarizing below DUV radiation and alignment of the polarization to a particular direction, and is also easily integrated with an r-θ sample stage.

Aside from grating height and width, more complicated profile structures can be measured by employing the recursive multiple layer RCW method herein discussed, using a staircase approximation of the grating shape. In other words, the grating is sliced into a number of rectangular slices, each of different width, and the multiple layer RCW calculation employed to compute the resulting diffraction efficiencies. The number of slices used is chosen so that the calculated diffraction efficiencies converge to the true diffraction efficiencies of the exact profile shape.

The parameters in the regression can be generalized and constrained, so that a complicated profile shape can be modeled and optimized without testing unnecessary and unphysical situations. For example, a trapezoidal shape can be characterized by a top width, bottom width, and total height. The model in this case actually consists of a stack of thin rectangular layers constrained to the trapezoidal shape, but otherwise forced to be consistent with the 3 parameters describing its shape. Therefore, the regression optimization only considers the three parameters describing the trapezoidal line shape. Even more complicated geometries can be approximated by stacking several such trapezoids on top of each other. Further constraint can be applied to the regression by requiring that the top width of the bottom trapezoid be the same as the bottom width of the next trapezoid in the stack, and so on. If the grating is symmetric with respect to rotations about the center of the ridges or grooves, the above reductions can be employed. Otherwise, the full RCW calculation may be used. In many cases, the real structure is approximately symmetric, so the grating model can be accordingly constrained, even if the profile shape is complicated. The above considerations can also be easily extended to structures having more than one transition per period and consist of more than just ridge and groove regions. For example, the grating ridges may have a sidewall coating.

With regard to eq. 1, in general, when measuring polarizing samples with a reflectometer eq. 1 can be used as long as the light incident on the system is unpolarized and the optical path itself does not impart an additional polarization dependence on either the incident or reflected light. As already mentioned, depolarizers can be used to counter the effects of polarizing optics or detection systems. Additionally, there are methods for constructing optical systems, such as placing successive mirrors in orthogonal optical planes, so that the effective polarization on the light is negligible, even when the individual optical components impart some polarization dependence.

An alternate technique disclosed herein might augment existing optical technologies operating with below DUV reflectometry data. One further technique could incorporate the normal incidence un-polarized below DUV reflectometer herein described with optical technologies that provide a larger data set, but operate in other wavelength regimes. For example, polarized DUV-Vis reflectance data could be combined with un-polarized VUV reflectance. The DUV-Vis reflectometer could operate at normal or non-normal angle of incidence, or even at multiple angles of incidence.

A below DUV ellipsometer, operating in the range from around 150 nm-800 nm or a DUV-Vis ellipsometer operating from about 200 nm-800 nm could be combined with the below DUV un-polarized reflectometer. The two datasets will compliment each other, and in some situations provide more information than either one dataset alone. The ellipsometer could be further modified to operate at multiple polar and azimuthal angles of incidence. Since the rigorous scattering methods can be used to determine ellipsometric data as well as reflectance data, such a combination could provide further decoupling when determining structural parameters of scattering surfaces.

Generally, the optical properties of the films involved in the patterned areas are characterized using similar, but un-patterned versions of the same film stacks. In some cases, the scribe area between patterned regions of a semiconductor wafer have the same film structure as the patterned features, except that they are not etched. If these areas are not present, specific un-patterned film test structures can be provided near the patterned features. If the test structures or scribe areas are close enough to the measured patterned areas, optical data from the two areas can be simultaneously analyzed and common properties of the areas constrained to be the same during the analysis. One particularly convenient way to implement this is through use of an imaging vacuum ultraviolet reflectometer of the type described in U.S. Pat. No. 7,067,818, since the reflectance data from the two areas can be simultaneously collected. Aside from simultaneously analyzing the data, the ratio of the reflectance data can also be advantageously used, since this ratio is independent of the incident intensity, thus removing the need to calibrate absolute reflectance of the reflectometer.

It will be recognized that the techniques described herein are not limited to a particular hardware embodiment of optical metrology tools but rather may be used in conjunction with a wide variety of types of hardware. Thus, the hardware described herein will be recognized as merely being exemplary. Further, it will be recognized that the techniques described herein may be utilized with a wide variety of types of computers, processors, computer systems, processing systems, etc. that may perform the various calculations provided herein in conjunction with collected data. Further, it will be recognized that the various techniques described herein may be implemented with software that may reside on a computer or machine readable medium. For instance the various calculations described herein may be accomplished through standard programming techniques with computer programs that operate on a computer, processor, computer system, processing system, etc.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein, and certain features of the invention may be utilized independently of the use of other features, all as would be apparent to one skilled in the art after having the benefit of this description of the invention.

What is claimed is:

1. A reflectometer apparatus for analyzing a scattering or diffracting structure, comprising:
 a below deep ultra-violet (DUV) wavelength referencing reflectometer configured for normal incidence operation and having a light source that provides light at wavelengths below 190 nm, wherein referencing is configured to account for system and environmental changes to adjust reflectance data obtained through use of the reflectometer; and
 at least one computer, which is connected to the reflectometer and is configured to run a computer program which causes the at least one computer to extract structural and optical parameters from a theoretical model of the scattering or diffracting structure, wherein the computer program uses a reduced RCW calculation for analyzing 2-D periodic structures of the scattering or diffracting structure.

2. The apparatus of claim 1, wherein an absolute reflectance of the below DUV wavelength referencing reflectometer is calibrated using reflectance ratios of two or more calibration samples in order to account for changing conditions of the calibration samples.

3. The apparatus of claim 1, wherein the computer program uses a group theoretic approach for analyzing 3-D periodic structures.

4. The apparatus of claim 1, wherein the light directed on the scattering or diffracting structure is un-polarized.

5. The apparatus of claim 4, further comprising an r-θ stage for holding the scattering or diffracting structure.

6. The apparatus of claim 5, wherein a calculated reflectance is obtained from a relationship $R=0.5*(R_{TE}+R_{TM})$, regardless of a sample rotation.

7. The apparatus of claim 1, wherein the reflectometer comprises at least one environmentally controlled chamber in which the light travels, the chamber sufficiently controlled to allow transmission of wavelengths below DUV light.

8. A method of optically measuring diffracting and scattering features on a sample, comprising:
providing an optical signal having at least some light at wavelengths below 190 nm;
directing the light on the sample in a substantially normally incident configuration, wherein the incident light is un-polarized;
utilizing a reduced RCW calculation to analyze 2-D periodic structures; and
utilizing a group theoretic approach to analyze 3-D periodic structures.

9. The method of claim 8, wherein the diffracting and scattering features on a sample are optically measured via a reflectometer having at least some light below deep ultra-violet wavelengths.

10. The method of claim 9, wherein referencing is utilized to account for system and environmental changes to adjust reflectance data obtained through use of the reflectometer.

11. The method of claim 9, wherein the absolute reflectance of the reflectometer is calibrated using reflectance ratios of two or more calibration samples in order to account for changes in calibration sample conditions.

12. The method of claim 8, wherein the reflectometer employs an r-θ stage.

13. The method of claim 12, wherein a calculated reflectance is obtained for 2-D and 3-D periodic structures from a relationship $R=0.5*(R_{TE}+R_{TM})$, regardless of sample rotation.

14. A method of optically measuring diffracting and scattering features on a sample, comprising:
providing a reflectometer that utilizes at least some light at wavelengths below 190 nm;
measuring intensity data from a plurality of sites within an area of the sample; and
analyzing a combination of the measured intensity data from the plurality of sites that is independent of incident intensity in order to extract structural and/or optical property information regarding the sample.

15. The method of claim 14, wherein at least one of the sites represents an un-patterned region of the sample and at least one other site represents a patterned region of the sample.

16. The method of claim 15, where at least one property of a patterned region film and one property of an un-patterned region film are common.

17. The method of claim 16, wherein the value of the at least one common property is coupled when analyzing the combination of the measured intensity data.

18. The method of claim 14, wherein the measured intensity data is obtained serially from at least two of the plurality of sites.

19. The method of claim 14, wherein a reflectance ratio between two or more of the sites is formed from the intensity data.

20. The method of claim 19, wherein the reflectance ratio is utilized at least in part to avoid calibrating an absolute reflectance of the reflectometer.

21. A method of optically measuring diffracting and scattering features on a sample, comprising:
providing a reflectometer that utilizes at least some light at wavelengths below 190 nm; and
measuring intensity data from a plurality of sites within an area of the sample; wherein at least one of the sites represents an un-patterned region of the sample and at least one other site represents a patterned region of the sample.

22. The method of claim 21, wherein a reflectance ratio between two or more of the sites is formed from the intensity data.

23. The method of claim 22, wherein the reflectance ratio is utilized at least in part to avoid calibrating an absolute reflectance of the reflectometer.

24. A reflectometer apparatus for analyzing a scattering or diffracting structure, comprising:
a below deep ultra-violet (DUV) wavelength referencing reflectometer configured for normal incidence operation and having an unpolarized light source and non-polarizing optical system that provides light at wavelengths below 190 nm, wherein referencing is configured to account for system and environmental changes to adjust reflectance data obtained through use of the reflectometer;
at least one computer, which is connected to the reflectometer and is configured to run a computer program which causes the at least one computer to extract structural and optical parameters from a theoretical model of the scattering or diffracting structure; and
an r-θ stage for holding the scattering or diffracting structure, wherein a calculated reflectance is obtained from a relationship that is independent of a sample rotation.

25. The apparatus of claim 24, wherein an absolute reflectance of the below DUV wavelength referencing reflectometer is calibrated using reflectance ratios of two or more calibration samples in order to account for changing conditions of the calibration samples.

26. The apparatus of claim 24, wherein the relationship is $R=0.5*(R_{TE}+R_{TM})$.

* * * * *